US010167308B2

(12) United States Patent
Srivastava et al.

(10) Patent No.: US 10,167,308 B2
(45) Date of Patent: *Jan. 1, 2019

(54) HIGHLY EFFICIENT SYNTHESIS OF LONG RNA USING REVERSE DIRECTION APPROACH

(71) Applicant: ChemGenes Corporation, Wilmington, MA (US)

(72) Inventors: Suresh C Srivastava, Burlington, MA (US); Naveen P Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,807

(22) Filed: Mar. 14, 2016

(65) Prior Publication Data

US 2016/0200759 A1    Jul. 14, 2016

Related U.S. Application Data

(63) Continuation of application No. PCT/US2014/055711, filed on Sep. 15, 2014.

(60) Provisional application No. 61/877,980, filed on Sep. 14, 2013.

(51) Int. Cl.
| C07H 1/00 | (2006.01) |
| C07H 21/02 | (2006.01) |
| C12Q 1/6806 | (2018.01) |
| C07H 21/00 | (2006.01) |

(52) U.S. Cl.
CPC ............. *C07H 21/02* (2013.01); *C07H 1/00* (2013.01); *C12Q 1/6806* (2013.01)

(58) Field of Classification Search
None
See application file for complete search history.

(56) References Cited

U.S. PATENT DOCUMENTS

| 8,324,368 B2 | 12/2012 | Gollob et al. |
| 2010/0324278 A1 | 12/2010 | Srivastava et al. |
| 2011/0137010 A1 | 6/2011 | Srivastava et al. |

OTHER PUBLICATIONS

Wagner et al. Helvetical Chimica Acta (2000), vol. 83, pp. 2023-2035.*
Sannes-Lowery et al. Trends in Analytical Chemistry (2000), vol. 19, pp. 481-491.*
Search Report in Chinese Application 200980144136.7, based on PCT/US2009/005063, which in turn is based on U.S. Appl. No. 61/191,065, Search Report dated Jul. 25, 2013 (Chinese Only).
First Office Action in Chinese Application 200980144136.7, based on PCT/US2009/005063, which in turn is based on U.S. Appl. No. 61/191,065, Office Action dated Aug. 6, 2013 (Chinese, with English Translation).
Suresh C. Srivastava et al., RNA Synthesis: Phosphoramidites for RNA synthesis in the reverse direction. Highly efficient synthesis and application to convenient introduction of ligands, chromophores and modifications of synthetic RNA at the 3'-end, Nucleic Acids Symposium Series No. 52, 103-104, Symposium Date: Sep. 8, 2008.
Vasulinga T. Ravikumar et al., Stereoselective Synthesis of Alkylphosphonates: A Facile Rearrangement of Cyanoethyl-Protected Nucleoside Phosphoramidites, Organic Process Research & Development, 2004, 8, 603-608.
M.E. Schwartz, et.al., A Universal Adapter for Chemical Synthesis of DNA or RNA on any Single Type of Solid Support, Tetrahedron Letters, vol. 36, No. 1, pp. 27-30, 1995.
International Preliminary Report on Patentability on PCT/US2009/005063, which in turn is based on U.S. Appl. No. 61/191,065, Report dated Mar. 8, 2011.
Japanese Office Action of Japanese application 2011-526061, which is based on PCT/US2009/005063, which in turn is based on U.S. Appl. No. 61/191,065, Office Action dated Mar. 19, 2014 (Japanese, with English Translation).
European Communication of European application 09789283.0, which is based on PCT/US2009/005063, which in turn is based on U.S. Appl. No. 61/191,065, Communication dated Jun. 24, 2014.
S. Matysiak et al., "Acetyl oligonucleotide Conjugates in Antisense Strategy", Nucleosides & Nucleotides, US, Marcel Dekker Inc., Jan. 1, vol. 16, 855-861 (1997).
T. Wagner et al., "Synthesis of 2'-Deoxyribonucleoside-5'-Phosphoramidites: New Building Blocks for the Inverse (5'-3')-Oligonucleotide Approach", Helvetica Chimica Acta, vol. 83, 2023-2035 (2000).
"RNA Synthesis by Reverse Direction Process: Phosphoramidites and High Purity RNAs and Introduction of Ligands, Chromophores, and Modifications at 3'-End" in Current Protocols in Nucleic Acid Chemistry, Jun. 2011, Unit 3.20.1-3.20.39, by Suresh Srivastava et al.
"Reverse Synthesis and 3'-Modification of RNA" in XX International Round Table on Nucleosides, Nucleotides and Nucleic Acids, International Society of Nucleosides, Nucleotides and Nucleic Acids (IS3NA) Aug. 5-9, 2012, Montreal, Canada, Poster Abstract, No. 64, by Lucas Bethge et al.
"Chemical and Structural Diversity of siRNA Molecules", Nawrot et al., Current Topics in Medicinal Chemistry, 2006, 6, 913-925.
Communication from U.S. Patent & Trademark Office, Office Action dated Jun. 18, 2015 for U.S. Appl. No. 14/568,066, a continuation application of U.S. Appl. No. 13/633,857, which is a continuation application of U.S. Appl. No. 12/584,625, which claims priority from U.S. Appl. No. 61/191,065.
European Patent Office Communication dated Apr. 4, 2017 in corresponding European Application EP 14844291, which is based on PCT/US2014/055711, which in turn is based on U.S. Appl. No. 61/877,980.

(Continued)

*Primary Examiner* — Patrick T Lewis
(74) *Attorney, Agent, or Firm* — Harvest IP Law LLP

(57) ABSTRACT

The present invention relates to novel process of reverse 5'→3' directed synthesis of RNA oligomers in the range of about 100-mer to about 200-mer has been developed and disclosed. Using that method demonstrated high quality RNA synthesis with coupling efficiency approaching 99%.

12 Claims, 10 Drawing Sheets

Specification includes a Sequence Listing.

(56) References Cited

OTHER PUBLICATIONS

Link Technologies Product Guide, 2010 (cited in European Patent Office Communication for European Application EP 14844291 as D6).

Nielsen, H., RNA Methods and Protocols, Humana Press (2011) (included on p. 13 of Applicant's response to Office Action dated May 3, 2017).

Strategies for Attaching Oligonucleotides to Solid Supports, Integrated DNA Technologies (2014) (included on p. 14 of Applicant's response to Office Action dated May 3, 2017).

\* cited by examiner 31-mer G-Rich RNA Chimera Synthesis (SEQ. ID No. 4)

Crude Purity by CE: 65.23 %

Trityl Bar Graph of 31-mer G-Rich RNA Chimera 43-mer RNA Synthesis (SEQ. ID No. 5)

Trityl bar graph of 43-mer G-Rich RNA Chimera

IE HPLC of Seq. ID- HS-5-2, Lot # 090712-1RE, Purity 93.5%

Seq. ID- HS-5-2, Lot # 090712-1RE, Calculated Mass; 14113.8

74-mer RNA Synthesis (Seq. ID No. 7)

Trityl bar graph of the 74-mer– Coupling time: 6 minutes

74mer RNA synthesized using Inverse RNA amidites;
Scale 10.0um; ESI/MS analysis Lane 1. Gel purified- 74mer
Lane 2. &
Lane 3. 74mer
RNA after RP
and IE HPLC purification

74mer RNA synthesized by Inverse RNA amidites;
Scale 10.0um; Gel analysis; Yield 10mg

76-mer RNA Synthesis (SEQ. ID No. 8)

Trityl bar graph of the 76-mer-- Coupling time: 6 minutes

PAGE of various RNAs (Crude desalted 76-mer) Synthesized

Lanes 1. Bromo phenol blue; 2. 76-mer with regular RNA; 3. 76-mer with reverse RNA; 4. 76-mer with reverse TOM RNA 100-mer RNA Synthesis (SEQ ID No. 1)

Trityl bar graph of the Poly-ribo Adenosine Oligonucleotide; Scale 1.0um ("5" represents 5'- phosphate)

150-mer RNA Synthesis (SEQ. ID No. 2)

Trityl bar graph of the Poly-ribo Adenosine Oligonucleotide; Scale 1.0um ("5" represents 5'- phosphate)

200-mer RNA Synthesis (SEQ. ID No. 3)

Trityl bar graph of the Poly-ribo Adenosine Oligonucleotide; Scale 1.0um (till 150mer) ("5" represents 5'- phosphate)

Trityl bar graph of the Poly-ribo Adenosine Oligonucleotide; Scale 0.5um
(from151 till 200mer)

UV Analysis of Poly-ribo Adenosine 200mer Oligonucleotide; Scale 0.5um

IE HPLC of the Poly-ribo Adenosine 100mer Oligonucleotide; Scale 1.0um

IE HPLC of the Poly-ribo Adenosine 150mer Oligonucleotide; Scale 1.0um

IE HPLC of the Poly-ribo Adenosine 200mer Oligonucleotide; Scale 0.5um

100mer & 200mer RNA Synthesis

Gel of Poly-Riboadenosine 100-mer & 200-mer Oligonucleotide:
E-Gel EX 2% Agarose

HIGHLY EFFICIENT SYNTHESIS OF LONG RNA USING REVERSE DIRECTION APPROACH

CROSS REFERENCE

This a Continuation Application filed under 35 U.S.C. § 111(a), claiming the benefit under 35 U.S.C. § 120 and § 365(c) of a PCT International Application PCT/US2014/055711, filed on Sep. 15, 2014, which in turn is a Patent Cooperation Treaty Application that is based on, and claims the benefit of U.S. Provisional Patent Application No. 61/877,980, filed Sep. 14, 2013, which is incorporated herein by reference in its entirety.

FIELD OF THE INVENTION

This invention relates to the synthesis of long RNA oligomers using monomer phosphoramidites, and corresponding solid supports that are suitable for RNA oligonucleotide synthesis in reverse 5'→3' direction. Particularly, this invention is directed using experimental conditions that are adaptable for the synthesis of long RNA oligomers from about 100-mers to about 200-mers.

BACKGROUND OF THE INVENTION

Defined sequence RNA synthesis in the 3'→5' direction is now well established and currently in use for synthesis and development of a vast variety of therapeutic grade RNA aptamers, tRNAs, siRNA and biologically active RNA molecules. This 3'→5' synthetic approach utilizes 3'-amidites and 3'-supports to lead to oligonucleotides.

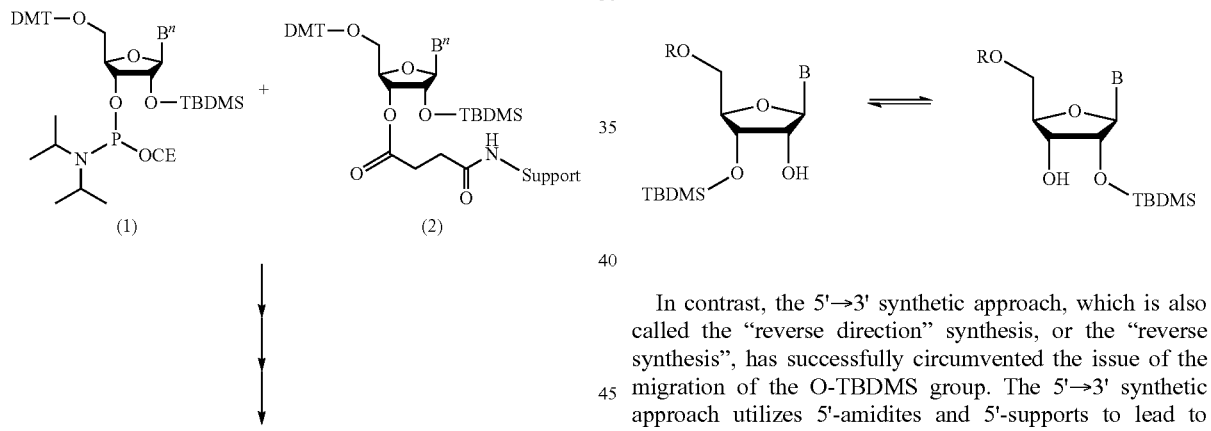

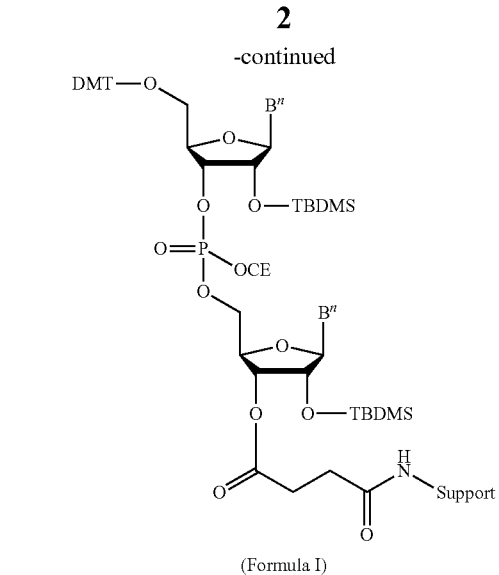

(Formula I)

However, the 3'→5' synthetic approach has a major draw back of the migration of the O-TBDMS group from the 3'-position to the 2'-position, and vice versa:

In contrast, the 5'→3' synthetic approach, which is also called the "reverse direction" synthesis, or the "reverse synthesis", has successfully circumvented the issue of the migration of the O-TBDMS group. The 5'→3' synthetic approach utilizes 5'-amidites and 5'-supports to lead to oligonucleotides, and can be summarized as:

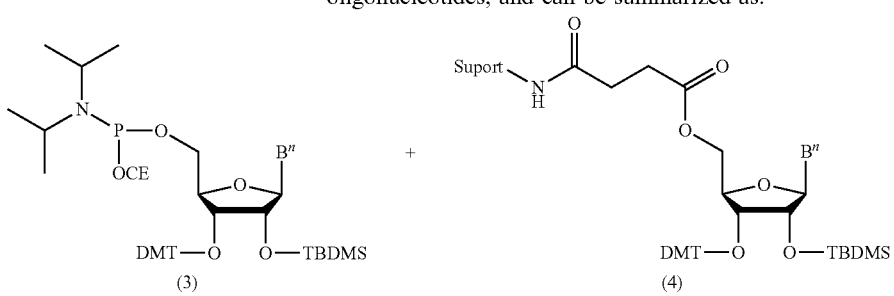

-continued

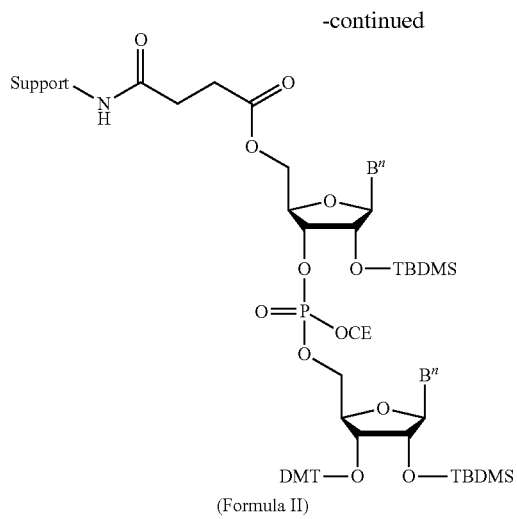

(Formula II)

The 5'→3' approach for RNA synthesis is documented in U.S. Pat. No. 8,309,707 and U.S. Pat. No. 8,541,569. By the 5'→3' approach, RNA's of various lengths have been successfully achieved, such as 31-mer, 43-mer, 74-mer and 76-mers. For instance:

A. 31-mer G-rich RNA Chimera Synthesis (Oligonucleotide containing 16 Guanosines) (see FIG. 1). The sequence is: 5'-ACG GGA AGA GGG AAmeU GAG GGmeU ACG AGG GCGme U-3' (SEQ. ID No. 4). Please note that "meU" is the modified base 2'-O-methyluridine.

B. 43-mer RNA Synthesis (see FIG. 2). The sequence is: GGC CCA UCC GUG GAG 988 876 77C CCA GGG 888 767 76C GGU C (SEQ. ID No. 5). Please note that:

"6" represents the modified base 2'-O-methyladenosine;
"7" represents the modified base 2'-O-methylcytidine;
"8" represents the modified base 2'-O-methylguanosine; and
"9" represents the modified base 2'-O-methyluridine.

C. 74-mer RNA Synthesis (see FIG. 3). The sequence is: UCC UCU GUA GUU CAG UCG GUA GAA CGG CGG ACU UUC AAU CCG UAU GUC ACU GGU UCG AGU CCA GUC AGA GGA GC (SEQ. ID No. 6).

D. 76-mer RNA Synthesis (see FIG. 4) The sequence is: GCC CGG AUA GCU CAG UCG GUA GAG CAU CAG ACU UUU UAU CUG AGG GUC CAG GGU UCA AGU CCC UGU UCG GGC GCC A (SEQ. ID No. 7)

However, there is a need to achieve the synthesis of longer RNA, such as 100-mer to 200-mer, especially in the application of the 5'→3' approach for the RNA synthesis.

Concurrently, several situations have made the research of longer RNA very crucial.

(A) Non-coding RNAs (ncRNAs) are known to regulate mammalian X-chromosome inactivation, and may also be processed to yield small RNAs (http://genesdev.cshlp org/content/23/13/1494.long).

(B) The RNA interference (RNAi) machinery has well-characterized roles in generation of microRNAs (miRNAs) and small interfering RNAs (siRNAs) that regulate gene expression post-transcriptionally. A 2.4-kb unspliced, polyadenylated nuclear-retained ncRNA known as mrhl is processed by Drosha to yield an 80-nt small RNA.

(C) Athough miRNAs and piwi-interfering RNAs (piRNAs) have received the most attention of late, that long RNA transcripts have important role in regulating the processing to small RNAs with likely different and unique functions.

(D) Long ncRNAs can be processed to yield small RNAs, but they can also affect how other transcripts are processed; for example, by modulating their ability to be cut into small RNAs or changing their pre-mRNA splicing patterns.

(E) ncRNA can inhibits the production of small RNAs from other transcripts.

(F) Non-Coding RNAs and Hormone regulation is an emerging field.

SUMMARY OF INVENTION

A process of synthesizing an RNA oligonucleotide of the following formula:

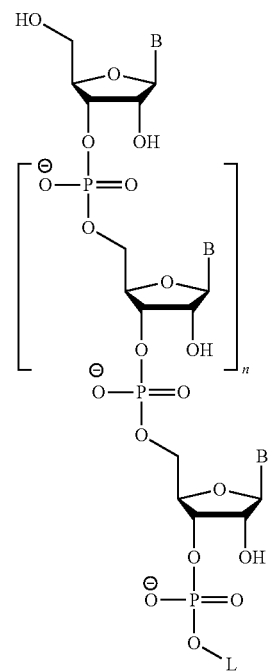

wherein:
B is a member selected from the group consisting of adenine, cytosine, guanine, uracil, 6-oxopurine, 5-methyl-cytosine, 5-methyl-uracil, 5-fluro-uracil, 7-deaza-adenine, 7-deaze-adenine and 5-fluro-cytosine;
n is an integer from 100 to about 200;
L is a nucleoside, a non-nucleoside ligand selected from the group consisting of cholesterol with a linker or a spacer, biotin, ethyleneglycol, glycerol, a polyethyelenglycol, a hexaehtyleneglycol, an amino linker, a disulfide linker, a peptide linker, a polypeptide linker, a protein, a flurophore, a quencher dye, one or more 2',5'-linked deoxynucleoside unit, one or more 2',5'-linked ribonucleoside unit, and one or more 2',5'-linked deoxyribose unit,
wherein L is attached at the 3'-end of the RNA nucleotide through an intervening phosphate; and the process of RNA is synthesized in a direction from the 5'-end to the 3'-end of the RNA nucleotide, and the process comprises the steps of:

(a) taking a nucleoside solid support represented by Formula 2:

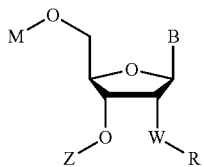

(Formula 2)

wherein:
M is a hydrogen radical or a linker;
  if M is a linker, then it is represented by the formula Y—C(O) and optionally connected to a solid support suitable for oligonucleotide synthesis,
  wherein Y is a hydrocarbon diradical moiety having a length between 2 carbons and 20 carbons, and Y is selected from the group consisting of alkyl, alkenyl, cycloalkyl, aryl, and aralkyl, and the hydrocarbon diradical moiety optionally comprises intervening —O—, —S—, —S(O)$_2$— —C(O)— and —NR$_6$— where R$_6$ is a hydrogen radical, or a substituted C$_1$ to C$_{20}$ alkyl or a substituted aralkyl;
W is selected from the group consisting of an oxygen diradical, an N—H diradical, and a fluorine radical, and R is selected so that:
  if W is an oxygen diradical, then R is tert butyl dimethyl silyl (TBDMS) or triisopropylsilyl oxymethylene (TOM); and
  if W is an N—H diradical, then R is of the form R$_5^x$, where x is selected from the group consisting of fluorenylmethyloxycarbonyl (Fmoc), trifluoroacetyl, acetyl, alkanoyl and aroyl; and
  if W is a fluorine radical, then R is not present;
B is selected from the group consisting of nucleoside base radicals consisting of 9-(N$^6$-benzoyladeninyl)-, 9-(N$^6$-acetyladeninyl)-, 9-(N$^6$-tert-butyl phenoxyacetyladeninyl)-, 9-(N$^6$-phenoxyacetyladeninyl)-, 9-(N$^6$-isopropyl phenoxyacetyladeninyl)-, 1-(N$^4$-benzoylcytosinyl)-, 1-(N$^4$-acetylcytosinyl)-, 1-(N$^4$—(N,N-dimethylformamidinyl)cytosinyl)-, 1-(N$^4$-phenoxyacetylcytosinyl)-, 1-(N$^4$-tert-butylphenoxyacetylcytosinyl)-, 1-(N$^4$-isopropyl phenoxyacetylcytosinyl)-, 9-(N$^2$-isobutylguaninyl)-, 9-(N$^2$-tert butyl phenoxyacetylguaninyl)-, 9-(N$^2$-isopropyl phenoxyacetylguaninyl)-, 1-(N$^4$-phenoxyacetylcytosinyl)-, 1-(N$^4$-tert butyl phenoxyacetylcytosinyl)-, 1-(N$^4$-isopropyl phenoxyacetylcytosinyl)-, and 1-uracilyl-; or
B is a modified nucleoside base radical selected from the consisting of 1-(N$^4$-benzoyl-5-methylcytosinyl)-, 1-(N$^4$—(N,N-dimethylformamidinyl)-5-methylcytosinyl)-, 1-(N$^4$-acetyl-5-methylcytosinyl)-, 1-(5-methyl-uracilyl)-, 1-(5-fluoro-uracilyl)-, 1-(N$^4$-benzoyl-5-fluorocytosinyl)-, 9-(N$^6$-benzoyl-7-deazaadeninyl)-, 9-(N$^6$—(N,N-dimethylformamidinyl)-7-deazaadenyl)-, 9-(N$^2$-isobutyl-7-deazaguaninyl)-, and 9-(N$^2$—(N,N-dimethylformamidinyl)-7-deazaguaninyl)-;
Z is a protecting group consisting of dimethoxy triphenyl (DMT), monomethoxy triphenyl (MMT) and trimethoxy triphenyl (TMT);

(b) placing a phosphoramidite represented by Formula 1 on a oligonucleotide synthesizer;

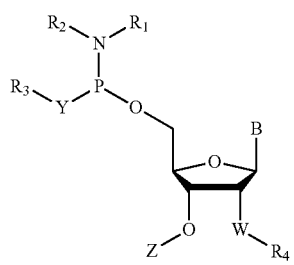

(Formula 1)

wherein
Y is an oxygen atom or a sulfur atom;
W is selected from the group consisting of an oxygen diradical, an N—H diradical, and a fluorine radical; and R$_4$ is selected so that:
  if W is an oxygen diradical, then R$_4$ is tert butyl dimethyl silyl (TBDMS) or triisopropylsilyl oxymethylene (TOM); and
  if W is an N—H diradical, then R$_4$ is of the form R$_5^x$, where x is selected from the group consisting of fluorenylmethyloxycarbonyl (Fmoc), trifluoroacetyl, acetyl, alkanoyl and aroyl; and
  if W is a fluorine radical, then R$_4$ is not present;
B is selected from the group consisting of nucleoside base radicals consisting of 9-(N$^6$-benzoyladeninyl)-, 9-(N$^6$-acetyladeninyl)-, 9-(N$^6$-tert-butyl phenoxyacetyladeninyl)-, 9-(N$^6$-phenoxyacetyladeninyl)-, 9-(N$^6$-isopropyl phenoxyacetyladeninyl)-, 1-(N$^6$—(N,N-dimethylformamidinyl)adeninyl)-, 1-(N$^4$-benzoylcytosinyl)-, 1-(N$^4$-acetylcytosinyl)-, 1-(N$^4$—(N,N-dimethylformamidinyl)cytosinyl)-, 1-(N$^4$-phenoxyacetylcytosinyl)-, 1-(N$^4$-tert-butylphenoxyacetylcytosinyl)-, 1-(N$^4$-isopropyl phenoxyacetylcytosinyl)-, 9-(N$^2$-isobutylguaninyl)-, 9-(N$^2$-tert butyl phenoxyacetylguaninyl)-, 9-(N$^2$-isopropyl phenoxyacetylguaninyl)-, 1-(N$^4$-phenoxyacetylcytosinyl)-, 1-(N$^4$-tert butyl phenoxyacetylcytosinyl)-, 1-(N$^4$-isopropyl phenoxyacetylcytosinyl)-, and 1-uracilyl-; or
B is a modified nucleoside base radical selected from the consisting of 1-(N$^4$-benzoyl-5-methylcytosinyl)-, 1-(N$^4$—(N,N-dimethylformamidinyl)-5-methylcytosinyl)-, 1-(N$^4$-acetyl-5-methylcytosinyl)-, 1-(5-methyl-uracilyl)-, 1-(5-fluoro-uracilyl)-, 1-(N$^4$-benzoyl-5-fluorocytosinyl)-, 9-(N$^6$-benzoyl-7-deazaadeninyl)-, 9-($N^6$—(N,N-dimethylformamidinyl)-7-deazaadenyl)-, 9-($N^2$-isobutyl-7-deazaguaninyl)-, and 9-($N^2$—(N,N-dimethylformamidinyl)-7-deazaguaninyl)-;

Z is a protecting group consisting of dimethoxy triphenyl (DMT), monomethoxy triphenyl (MMT) and trimethoxy triphenyl (TMT);

$R_1$ is an alkyl or aryl radical;

$R_2$ is an alkyl or aryl radical; and $R_3$ is cyanoethyl, alkyl or aryl radical.

B is hydrogen or a nucleobase which is optionally functionalized at each primary amine with an amine protecting group.

(c) removing the protecting group Z from the nucleoside solid support represented by Formula 2;

(d) performing the process of RNA synthesis by coupling the nucleoside of Formula 2 and the phosphoramidite of Formula 1 in the oligonucleotide synthesizer using a mixture of ancillary regents to result in an oligonucleotide having at least one protecting group;

(d) providing a phosphoramidite with an L group;

(e) adding the phosphoramidite with the L group at the end of the oligonucleotide to result in an oligonucleotide having the L group;

(f) detaching the oligonucleotide having the L group from the solid support;

(g) removing the at least one protecting group from the oligonucleotide;

(h) removing a silyl protecting group to result in the oligonucleotide;

(i) precipitating the oligonucleotide; and (j) analyzing the oligonucleotide for purity determination, wherein the ancillary reagent comprises CAP A (phenoxy acetic anhydride/tetrahydrofuran/pyridine), CAP B (10% N-methylimidazole/tetrahydrofuran), DMT removal reagent (3% TCA in toluene), oxidation solution (0.05 M iodine/pyridine/water/tetrahyrofuran) and activating reagent (5-ethylthio-1-H-tetrazole at 0.35 M in acetonitrile).

The process of synthesizing an RNA oligonucleotide, wherein L is cholesterol with the linker or the spacer, and n is an integer from 100 to about 200.

The process of synthesizing an RNA oligonucleotide, wherein L is polyethyleneglycol (PEG), and n is an integer from 100 to about 200.

An RNA oligonucleotide, wherein the RNA oligonucleotide is synthesized by the process of synthesizing an RNA oligonucleotide.

A method of RNA synthesis of 100-mer to about 200-mer long chain RNA using reverse RNA synthesis methodology.

A long chain RNA chimera, comprising deoxy, backbone-modified bases, modified DNA and modified RNA bases.

A long chain RNA having one or more 5', 2', 2',3' linkage at the terminals, at a branch point or within chain using reverse methodology.

A long chain RNA consisting of natural and modified nucleosides, abasic sites, reverse abasic sites, chromophores and ligands using reverse synthesis methodology.

A long chain RNA may include a chromophore, a ligand, a monophosphate, diphosphate or a triphosphate group using the reverse synthesis methodology.

A long chain RNA having branch point with one or more deoxy, modified deoxy or modified ribonucleoside using reverse RNA methodology.

A method of purification of Long chain RNA synthesized by reverse methodology by HPLC Gel electrophoresis or other RNA purification techniques.

A method of labeling and attachment of long chain RNA synthesized by reverse methodology on to a surface.

A method of using long chain RNA synthesized by reverse methodology in molecular biology research and development.

DETAILED DESCRIPTION OF THE INVENTION

Figure 1:
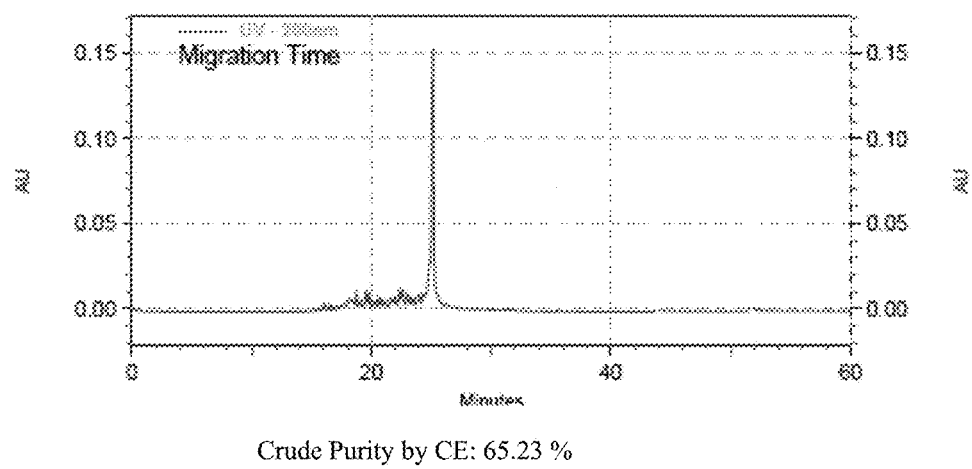
FIG. 1 is directed to a 31-mer RNA synthesis.
Figure 1:
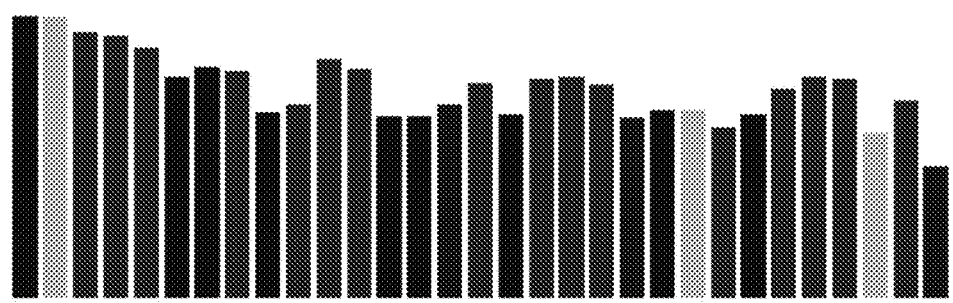
Figure 2:
FIG. 2 is directed to a 43-mer RNA synthesis.
Figure 2:
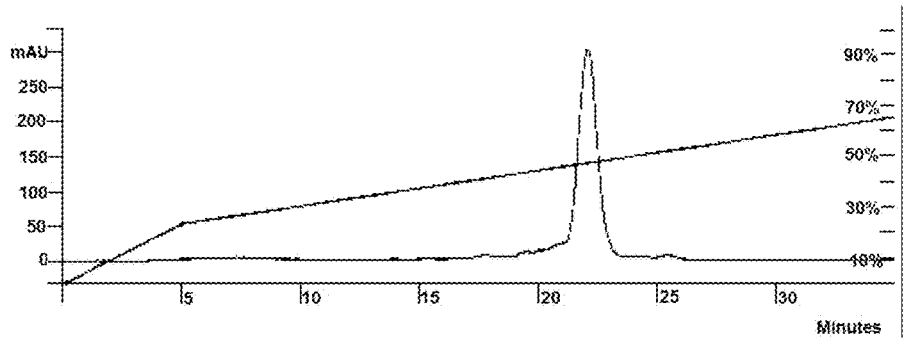
Figure 2:
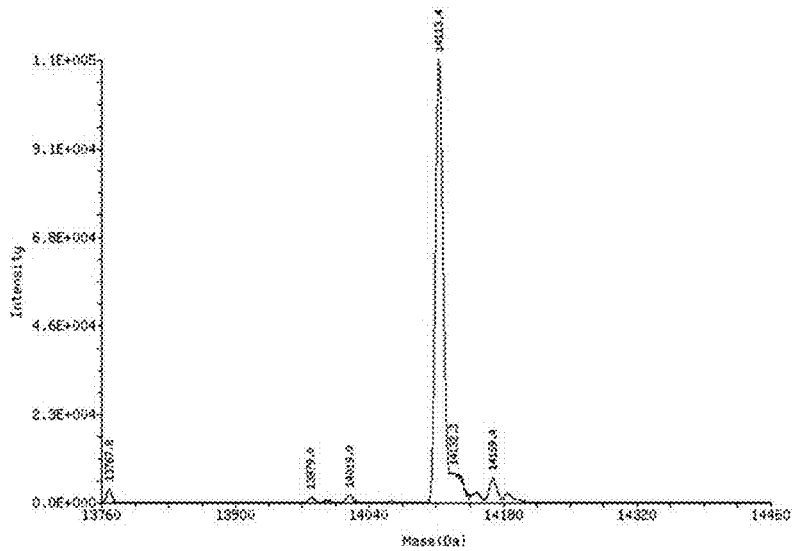
Figure 3:
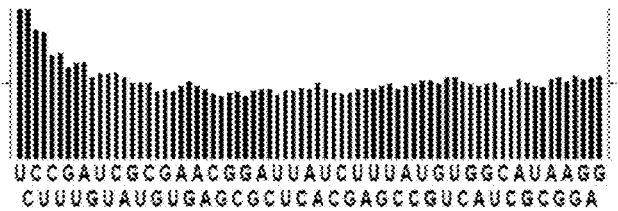
FIG. 3 is directed to a 74-mer RNA synthesis.
Figure 3:
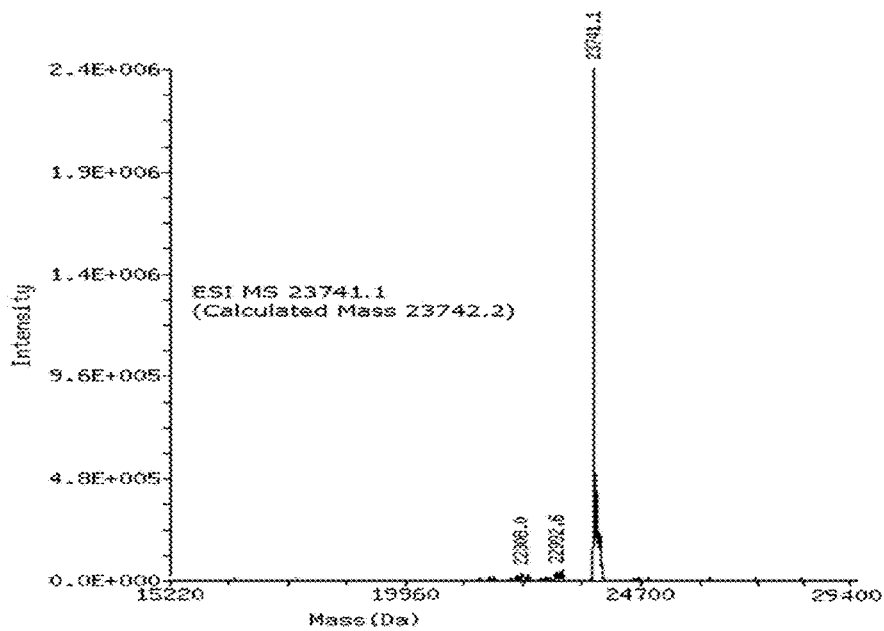
Figure 3:
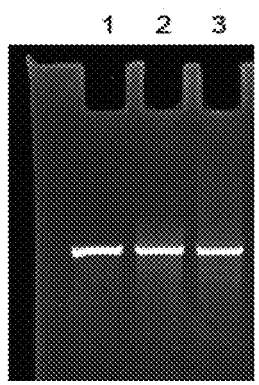
Figure 4:
FIG. 4 is directed to a 76-mer RNA synthesis.
Figure 4:
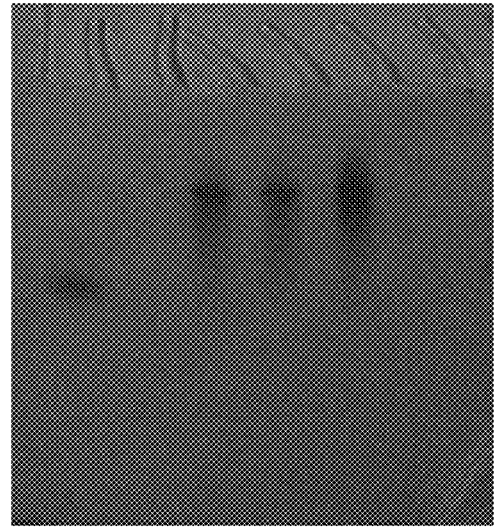

The invention is generally related to "long RNA", which is commonly accepted as RNA oligonucleotide that is at least about 100-mer, and can be about 200-mer or even longer. The terms "long RNA" and "extra long RNA" are used interchangeably throughout the invention.

To achieve the synthesis of long RNA in the range of about 100-mer to about 200-mer, a highly efficient coupling and a reduced coupling time are both crucial.

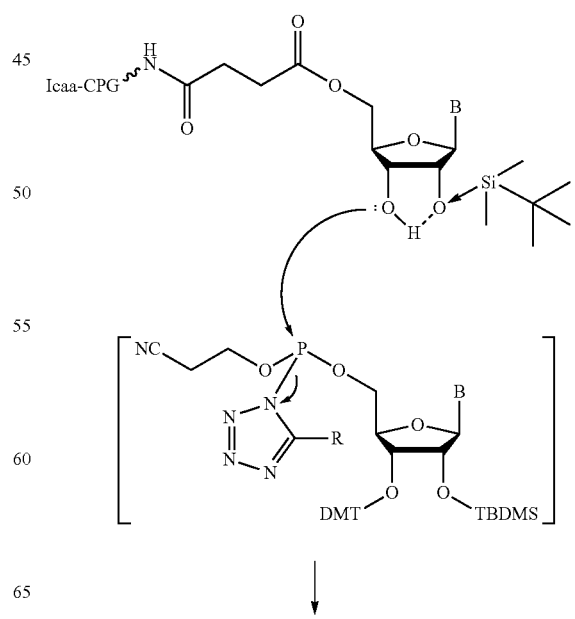

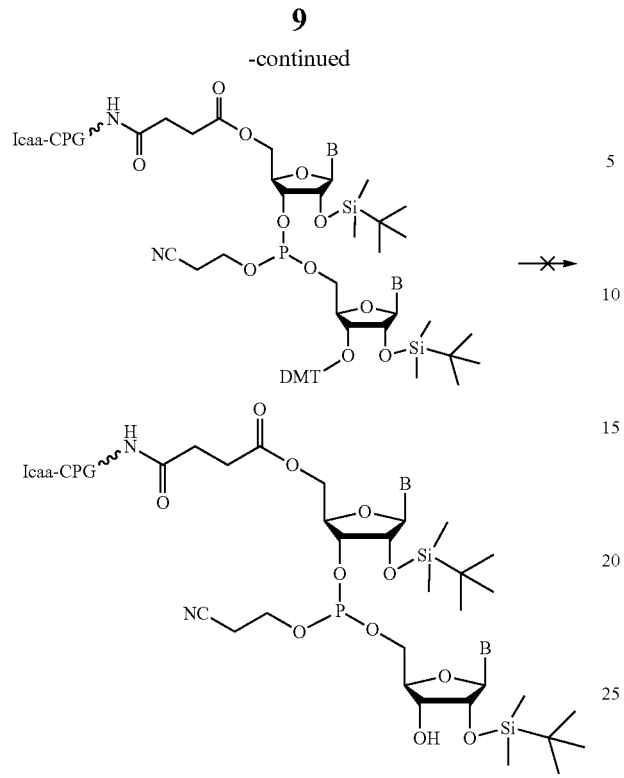

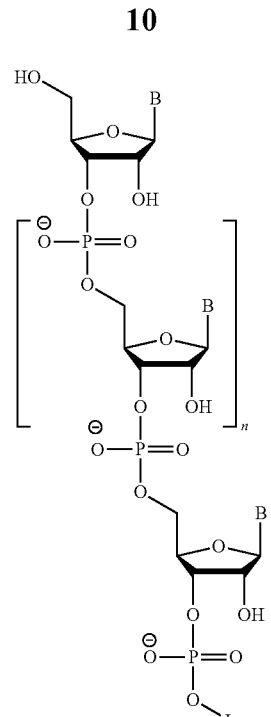

The use of a novel combination of ancillary agents in the process is crucial to achieve the synthesis of long RNA in the range of about 100-mer to about 200-mer. The details of the experiments are described below.

TABLE 1

Synthesis of Poly-Ribo Adenosine oligonucleotide 100-mer, 150-mer and 200-mer

| Seq. #1 (SEQ. ID No. 1) | 5rArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArA |
|---|---|
| Seq. #2 (SEQ. ID No. 2) | 5rArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArA |
| Seq. #3 (SEQ. ID No. 3) | 5rArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArArA | wherein "5" represents the 5'-terminal phosphate

According to the invention, the process of synthesizing an RNA oligonucleotide in the 5' to 3' direction is directed to the RNA oligonucleotide of the following formula:

wherein:
B is a member selected from the group consisting of adenine, cytosine, guanine, uracil, 6-oxopurine, 5-methyl-cytosine, 5-methyl-uracil, 5-fluro-uracil, 7-deaza-adenine, 7-deaze-adenine and 5-fluro-cytosine;
n is an integer from 100 to about 200;
L is a nucleoside, a non-nucleoside ligand selected from the group consisting of cholesterol with a linker or a spacer, biotin, ethyleneglycol, glycerol, a polyethyelenglycol, a hexaehtyleneglycol, an amino linker, a disulfide linker, a peptide linker, a polypeptide linker, a protein, a flurophore, a quencher dye, one or more 2',5'-linked deoxynucleoside unit, one or more 2',5'-linked ribonucleoside unit, and one or more 2',5'-linked deoxyribose unit,
wherein L is attached at the 3'-end of the RNA nucleotide through an intervening phosphate.

The process of RNA is synthesized in a direction from the 5'-end to the 3'-end of the RNA nucleotide, and the process includes the following steps:
(a) taking a nucleoside solid support represented by Formula 2:

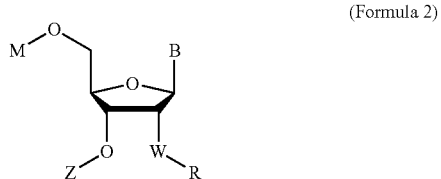

(Formula 2)

wherein:
M is a hydrogen radical or a linker;
if M is a linker, then it is represented by the formula Y—C(O) and optionally connected to a solid support suitable for oligonucleotide synthesis, wherein Y is a hydrocarbon diradical moiety having a length between 2 carbons and 20 carbons, and Y is selected from the group consisting of alkyl, alkenyl, cycloalkyl, aryl, and aralkyl, and the hydrocarbon diradical moiety optionally comprises intervening —O—, —S—, —S(O)$_2$— —C(O)— and —NR$_6$— where R$_6$ is a hydrogen radical, or a substituted C$_1$ to C$_{20}$ alkyl or a substituted aralkyl;

W is selected from the group consisting of an oxygen diradical, an N—H diradical, and a fluorine radical, and R is selected so that:

if W is an oxygen diradical, then R is tert butyl dimethyl silyl (TBDMS) or triisopropylsilyl oxymethylene (TOM); and if W is an N—H diradical, then R is of the form $R_5^x$, where x is selected from the group consisting of fluorenylmethyloxycarbonyl (Fmoc), trifluoroacetyl, acetyl, alkanoyl and aroyl; and if W is a fluorine radical, then R is not present;

B is selected from the group consisting of nucleoside base radicals consisting of 9-(N$^6$-benzoyladeninyl)-, 9-(N$^6$-acetyladeninyl)-, 9-(N$^6$-tert-butyl phenoxyacetyladeninyl)-, 9-(N$^6$-phenoxyacetyladeninyl)-, 9-(N$^6$-isopropyl phenoxyacetyladeninyl)-, 1-(N$^6$—(N,N-dimethylformamidinyl)adeninyl)1-(N$^4$-benzoylcytosinyl)-, 1-(N$^4$-acetylcytosinyl)-, 1-(N$^4$—(N,N-dimethylformamidinyl)cytosinyl)-, 1-(N$^4$-phenoxyacetylcytosinyl)-, 1-(N$^4$-tert-butylphenoxyacetylcytosinyl)-, 1-(N$^4$-isopropyl phenoxyacetylcytosinyl)-, 9-(N$^2$-isobutylguaninyl)-, 9-(N$^2$-tert butyl phenoxyacetylguaninyl)-, 9-(N$^2$-isopropyl phenoxyacetylguaninyl)-, 1-(N$^4$-phenoxyacetylcytosinyl)-, 1-(N$^4$-tert butyl phenoxyacetylcytosinyl)-, 1-(N$^4$-isopropyl phenoxyacetylcytosinyl)-, and 1-uracilyl-; or B is a modified nucleoside base radical selected from the consisting of 1-(N$^4$-benzoyl-5-methylcytosinyl)-, 1-(N$^4$—(N,N-dimethylformamidinyl)-5-methylcytosinyl)-, 1-(N$^4$-acetyl-5-methylcytosinyl)-, 1-(5-methyl-uracilyl)-, 1-(5-fluoro-uracilyl)-, 1-(N$^4$-benzoyl-5-fluorocytosinyl)-, 9-(N$^6$-benzoyl-7-deazaadeninyl)-, 9-(N$^6$—(N,N-dimethylformamidinyl)-7-deazaadenyl)-, 9-(N$^2$-isobutyl-7-deazaguaninyl)-, and 9-(N$^2$—(N,N-dimethylformamidinyl)-7-deazaguaninyl)-;

Z is a protecting group consisting of dimethoxy triphenyl (DMT), monomethoxy triphenyl (MMT) and trimethoxy triphenyl (TMT);

(b) placing a phosphoramidite represented by Formula 1 on a oligonucleotide synthesizer;

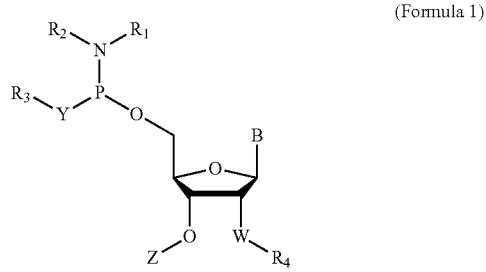

(Formula 1)

wherein

Y is an oxygen atom or a sulfur atom;

W is selected from the group consisting of an oxygen diradical, an N—H diradical, and a fluorine radical; and R$_4$ is selected so that:

if W is an oxygen diradical, then R$_4$ is tert butyl dimethyl silyl (TBDMS) or triisopropylsilyl oxymethylene (TOM); and if W is an N—H diradical, then R$_4$ is of the form $R_5^x$, where x is selected from the group consisting of fluorenylmethyloxycarbonyl (Fmoc), trifluoroacetyl, acetyl, alkanoyl and aroyl; and if W is a fluorine radical, then R$_4$ is not present;

B is selected from the group consisting of nucleoside base radicals consisting of 9-(N$^6$-benzoyladeninyl)-, 9-(N$^6$-acetyladeninyl)-, 9-(N$^6$-tert-butyl phenoxyacetyladeninyl)-, 9-(N$^6$-phenoxyacetyladeninyl)-, 9-(N$^6$-isopropyl phenoxyacetyladeninyl)-, 1-(N$^6$—(N,N-dimethylformamidinyl)adeninyl)1-(N$^4$-benzoylcytosinyl)-, 1-(N$^4$-acetylcytosinyl)-, 1-(N$^4$—(N,N-dimethylformamidinyl)cytosinyl)-, 1-(N$^4$-phenoxyacetylcytosinyl)-, 1-(N$^4$-tert-butylphenoxyacetylcytosinyl)-, 1-(N$^4$-isopropyl phenoxyacetylcytosinyl)-, 9-(N$^2$-isobutylguaninyl)-, 9-(N$^2$-tert butyl phenoxyacetylguaninyl)-, 9-(N$^2$-isopropyl phenoxyacetylguaninyl)-, 1-(N$^4$-phenoxyacetylcytosinyl)-, 1-(N$^4$-tert butyl phenoxyacetylcytosinyl)-, 1-(N$^4$-isopropyl phenoxyacetylcytosinyl)-, and 1-uracilyl-; or B is a modified nucleoside base radical selected from the consisting of 1-(N$^4$-benzoyl-5-methylcytosinyl)-, 1-(N$^4$—(N,N-dimethylformamidinyl)-5-methylcytosinyl)-, 1-(N$^4$-acetyl-5-methylcytosinyl)-, 1-(5-methyl-uracilyl)-, 1-(5-fluoro-uracilyl)-, 1-(N$^4$-benzoyl-5-fluorocytosinyl)-, 9-(N$^6$-benzoyl-7-deazaadeninyl)-, 9-(N$^6$—(N,N-dimethylformamidinyl)-7-deazaadenyl)-, 9-(N$^2$-isobutyl-7-deazaguaninyl)-, and 9-(N$^2$—(N,N-dimethylformamidinyl)-7-deazaguaninyl)-;

Z is a protecting group consisting of dimethoxy triphenyl (DMT), monomethoxy triphenyl (MMT) and trimethoxy triphenyl (TMT);

R$_1$ is an alkyl or aryl radical;

R$_2$ is an alkyl or aryl radical; and

R$_3$ is cyanoethyl, alkyl or aryl radical.

B is hydrogen or a nucleobase which is optionally functionalized at each primary amine with an amine protecting group;

(c) removing the protecting group Z from the nucleoside solid support represented by Formula 2;

(d) performing the process of RNA synthesis by coupling the nucleoside of Formula 2 and the phosphoramidite of Formula 1 in the oligonucleotide synthesizer using a mixture of ancillary regents to result in an oligonucleotide having at least one protecting group;

(d) providing a phosphoramidite with an L group;

(e) adding the phosphoramidite with the L group at the end of the oligonucleotide to result in an oligonucleotide having the L group;

(f) detaching the oligonucleotide having the L group from the solid support;

(g) removing the at least one protecting group from the oligonucleotide;

(h) removing a silyl protecting group to result in the oligonucleotide;

(i) precipitating the oligonucleotide; and (j) analyzing the oligonucleotide for purity determination.

The ancillary reagent comprises CAP A (phenoxy acetic anhydride/tetrahydrofuran/pyridine), CAP B (10% N-methylimidazole/tetrohydrofuran), DMT removal reagent (3% TCA in toluene), oxidation solution (0.05 M iodine/pyridine/water/tetrahyrofuran) and activating reagent (5-ethyl-thio-1-H-tetrazole at 0.35 M in acetonitrile).

According to the invention, a long RNA is an RNA oligomer having 100 to 200 monomers. To achieve this goal, the ancillary reagents are crucial to this process. In a reverse synthesis of RNA, that is, from the 5'- to the 3'-direction, ancillary reagents are usually a combination of TCA/DCM, DCA/DCM, TCA/toluene, DCA/toluene, anhydrous acetonitrile, CAP A, CAP B, Iodine/THF/pyridine/H2O of various concentrations, one of the appropriate sulfurizing reagents, one of the appropriate activating reagent as acetonitrile solution.

The ancillary reagents being utilized for this invention are helpful as they allow high coupling of the monomer-5'-amidites to completion. Therefore, the ancillary reagents such as 0.3 M BMT (5-benzylthiotetrazole) or 0.5 M ETT (5-thioethyltetrazole) in shorter coupling time are specifically pertinent and use different coupling time and produce unique results of high coupling efficiency as compared to the same reagents that have been employed for shorter RNA oligomers.

According to an embodiment of the invention, L is cholesterol with the linker or the spacer, and n is an integer from 100 to about 200.

In another embodiment of the invention, L is polyethyleneglycol (PEG), and n is an integer from 100 to about 200.

Another embodiment of the invention is related to an RNA oligonucleotide with n=100, 150 or about 200 that is synthesized by the above process. Because the RNA oligonucleotide is synthesized in the 5' to the 3' direction, impurities that are referred to as "m+1" species are not present.

From our data on oligonucleotides having a 3'-cholesterol conjugation at the the 3'-end synthesized by both methodologies, viz., 3'→5' direction and 5'→3' direction can be clearly seen as in our published patents.

Another embodiment of the invention is related to a method of RNA synthesis of 100-mer to 200-mer long chain RNA using reverse RNA synthesis methodology.

The invention also includes a long chain RNA chimera, comprising deoxy, backbone-modified bases, modified DNA and modified RNA bases. The long chain RNA having one or more 5', 2', 2',3' linkage at the terminals, at a branch point or within chain using reverse methodology.

According to the invention, another embodiment is a long chain RNA including natural and modified nucleosides, abasic sites, reverse abasic sites, chromophores and ligands using reverse synthesis methodology.

Another embodiment of the invention is a long chain RNA comprising a chromophore, ligand, monophosphate, diphosphate or triphosphate group using reverse synthesis methodology.

Yet another embodiment of the invention is a long chain RNA having a branch point with one or more deoxy-, modified deoxy or modified ribonucleoside using reverse RNA methodology.

Furthermore, the invention includes a method of purification of Long chain RNA synthesized by reverse methodology by HPLC Gel electrophoresis or other RNA purification techniques.

The invention also includes a method of labeling and attachment of long chain RNA synthesized by reverse methodology on to a surface, such as various kind of chips, polyethylene glycols, supports via the 3'-end of the oligonucleotide synthesized. Thus introduction of functional groups such as amine function to the oligonucleotide will allow attachment to chips or surfaces contained an aldehyde function.

The invention further includes a method of using long chain RNA synthesized by reverse methodology in molecular biology research and development. The RNA synthesized by the process according to the invention have been shown to possess biochemical properties which is distinguishing from the RNA synthesized by normal process of 3'→5'-direction.

Oligonucleotide Synthesis: The oligonucleotides Seq. #1 (SEQ ID No.1) (100-mer), Seq. #2 (SEQ. ID No. 2)(150-mer), Seq. #3 SEQ. ID No. 3 are synthesized. Seq. #2 was extended up to 200-mer) were synthesized using 5'→3' directed REV-RNA phosphoramidite chemistry in 1 micromole scale, except Seq. #3. Seq. #3 was synthesized 0.5 vmole scale. The synthesis were performed on Expedite 8900 synthesizer using standard RNA 1 vmole cycle and coupling time of the monomers with solid support 6.0 minute. In oligonucleotides synthesis 5 is represent the Universal UnyLinker support 3000A, ChemGenes Cat # N-4000-30.

(1) Amidites used $N^6$-tbpac-2'-O-TBDMS-3'-O-DMT-adenosine-5'-cyanoethyl-N,N-diisopropyl-phosphoramidite. LOT # AT 239-9(ChemGenes Cat # ANP-3407)

(2) CPG used Universal UnyLinker support 3000A, ChemGenes Cat # N-4000-30, Lot # AT157-9

(3) Ancillary reagent used

Anhydrous Acetonitrile RN-1447

CAP A (Phenoxy Acetic Anhydride/THF/Pyridine)

CAP B (10% N-Methylimidazole/THF)

DMT Removal Reagent (3% TCA in Toluene)

Oxidation Solution (0.05M Iodine/Pyridine/$H_2O$/THF)

Activation Reagent, 5-Ethylthio-1-H-Tetrazole (ETT) (0.35M in Acetonitrile)

First take the amidite in 60 ml expedite bottle and dissolve in dry acetonitrile to make the solution 0.15M. After that, attach the monomer bottle to the synthesizer on port # A.

Following synthesis, the controlled pore glass (CPG) solid support was washed with 3.0 ml diethyl ether and transferred to a 2 ml microfuge tube. Oligonucleotides were cleaved from the CPG and deprotected by incubation for Seq. #1, 45 min at 65° C. in 1.2 ml of 33% methylamine in absolute ethanol (Aldrich Cat #534102-250ML, Lot # SHBC2933V).

For Seq. #2 & 3, 90 min at 65° C. in 1.2 ml of 33% methylamine in absolute ethanol (Aldrich Cat #534102-250ML, Lot # SHBC2933V). After that, cool down the tubes at −20° C. for 30 minute. Then the supernatant was removed and the CPG was washed with 500 ul of water; supernatants were pooled and dried on speed vac. The t-butyl-dimethylsilyl protecting group was removed from the RNA residue by treatment with 1000 ul of triethylamine hydrofluoride (Oakwood chemical, Cat #003029, Lot # F29E), at 45° C. in ultrasonic bath for 4 hours. The oligonucleotide was precipitated by 3.0 ml of n-butanol; the sample was cooled at −20° C. for 1 hour then centrifuged at 5,000 g for 10 minutes. The supernatant was decanted, and the pellet was washed with n-butanol one more time. Finally washed with 500 ul acetonitrile and then again centrifuge at 5000 rpm for 5 minutes, the supernatant was decanted. The pellet was dissolve in 1000 ul M.Q water and check the OD's (Crude desalt).

The oligonucleotides were then purified by Ion-Exchange HPLC using a linear gradient of sodium perchlorate in buffer A=(5.0%, 1.0M TRIS and 10.0% Methanol) pH 7.5. Buffer B=0.5M Sodium perchlorate in buffer A.

The entire sample was loaded on a Source15Q column (1.0 cm×25 cm) and eluted with a linear 0% to 85% sodium perchlorate gradient over 40 minutes. Samples were monitored at 295 nm and peaks corresponding to the desired oligonucleotide species were collected, and precipitated by adding 5.0 volume of (2% LiClO$_4$ in acetone), followed by centrifuging at 5,000 g for 10 minutes. The supernatant was decanted; the pellet was washed with ethanol.

Figure 5:
FIG. 5 is the trityl bar of the 100-mer synthesis.

The trityl bar graph of the 100-mer RNA synthesis is presented in FIG. 5. It can be seen that trityl bar graph denotes that coupling efficiency per step of the oligo proceeds in consistent manner and there is no drop of coupling as the chain length grows.

Figure 6:
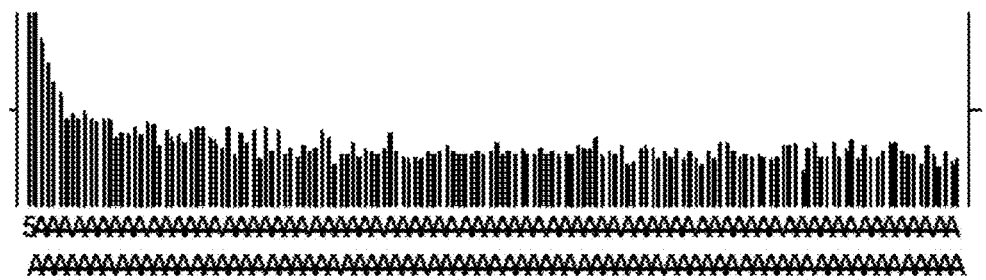
FIG. 6 is the trityl bar of the 150-mer synthesis.

The trityl bar graph of the 150-mer RNA synthesis is presented in FIG. 6. It can be observed from the bar graph that the synthesis of 150-mer is proceeding consistently and smoothly without any significant drop.

Figure 7:
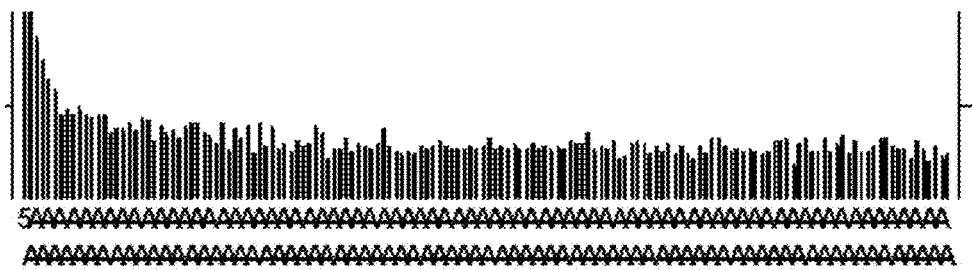
FIG. 7 is the trityl bar of the 200-mer synthesis.
Figure 7:
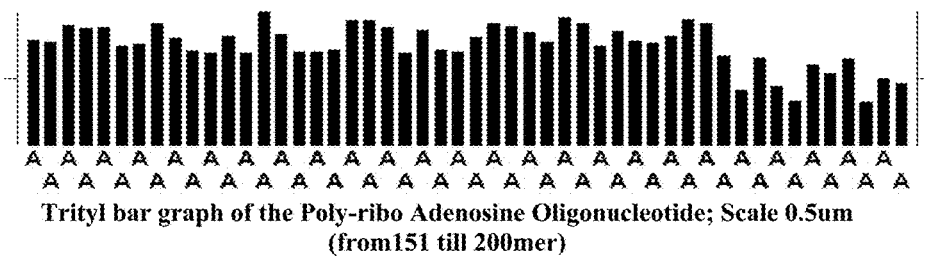
Figure 8:
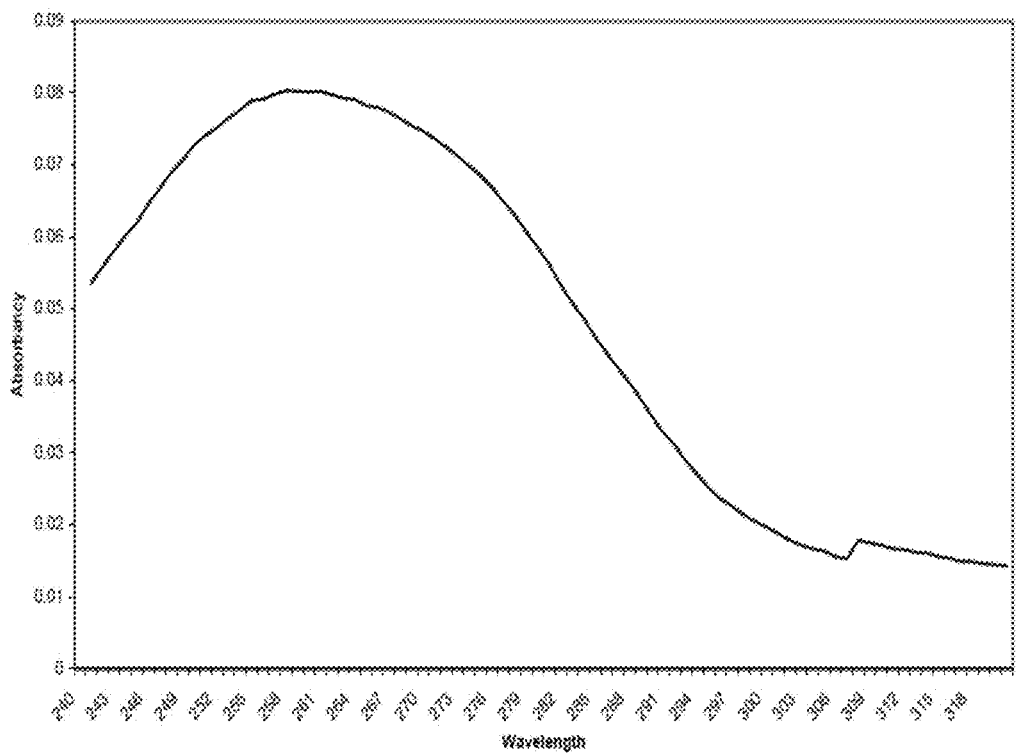
FIG. 8 is the UV analysis of the 200-mer synthesis.

The trityl bar graph of the 200-mer RNA synthesis is presented in FIG. 7. It can be observed that even for the oligo nucleotide of such a long length, the coupling efficiency per step proceeds in consistent manner and there is no significant drop of coupling as the chain length grows.

Figure 9:
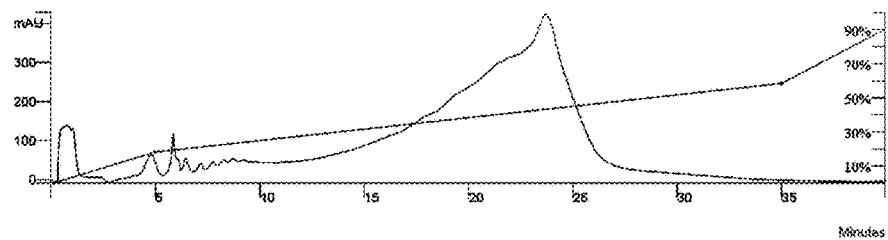
FIG. 9 is the IE HPLC of the poly-ribo adenosine 100-mer synthesis, the IE HPLC of the poly-ribo adenosine 150-mer synthesis, and the IE HPLC of the poly-ribo-adenosine 200-mer synthesis.
Figure 9:
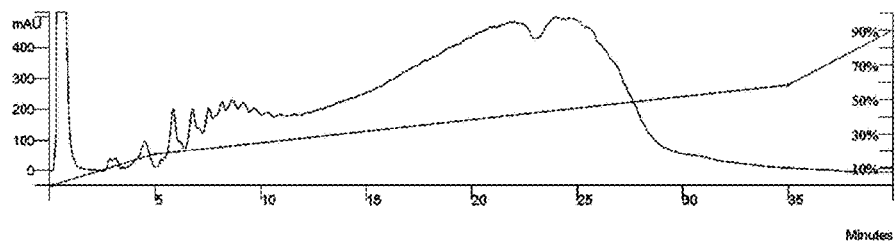
Figure 9:
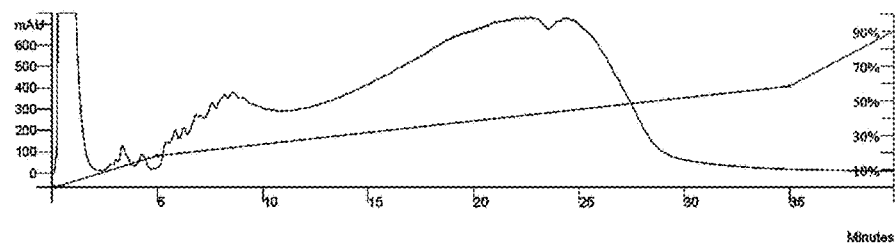

The IE HPLC of the 100-mer synthesis, the 150-mer synthesis and the 200-mer synthesis (FIG. 9): The 100-mer crude synthesized at 1.0 umole scale as expected shows broad peak in expected elution time. The IE HPLC of 150-mer crude oligonucleotide, as expected, still shows broader peak in expected elution time. The IE HPLC of 200-mer is still broader peak and elutes in expected elution time.

Figure 10:
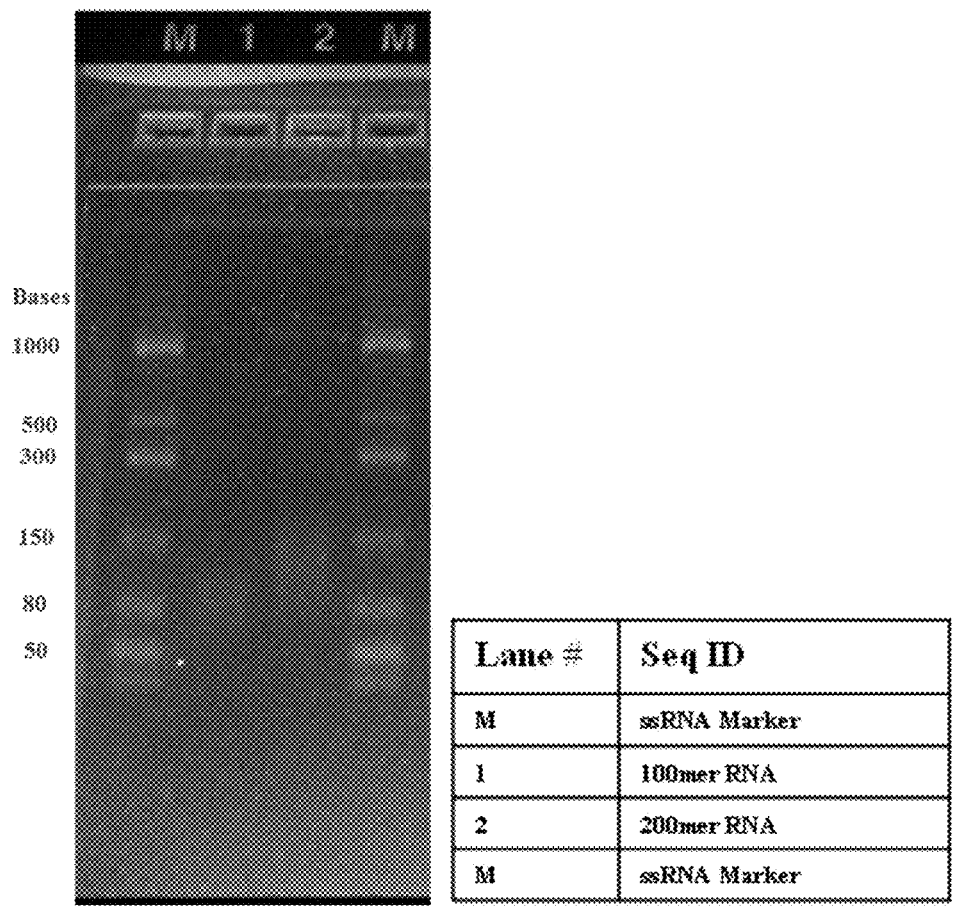
FIG. 10 is the gel of poly-ribo-adenosine 100-mer and 200-mer oligonucleotides.

The gel of the 100-mer and the 200-mer RNA synthesis (FIG. 10) shows a band for 100-mer migrating slightly slower than 80-mer marker. The 200-mer was seen migrating slower than 100-mer and further slower than 150-mer.

The reverse RNA monomer phosphoramidites in the present invention carry a 3'-DMT group in ribonucleosides, carrying 2'-tBDsilyl (tBDSi)-5'-cyanoethylphosphoramidite (CED) (Structure 16), 3'-DMT-2'-tBDsilyl-5'-succinyl-Icaa CPG-n-protected nucleosides (Structure 17) or 3'-DMT-2'-triisopropylsilyloxymethyl (TOM)-5'-CED phosphoramidite group (Structure 18).

Structure (16)

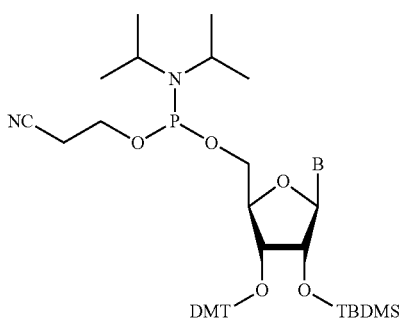

Where B = A (N-Bz), C (N-Bz), C (N-Ac), G (N-iBu),
A (N-tBPac), C (N-tBPac), C (N-tBPac), G (N-tBPac),
A (N-Pac), C (N-Pac), C (N-Pac), G (N-Pac), U.

3'-DMT-2'-tBDSilyl-5'-Amidites
(Reverse RNA-tBDsilyl-amidities)

Structure (17)

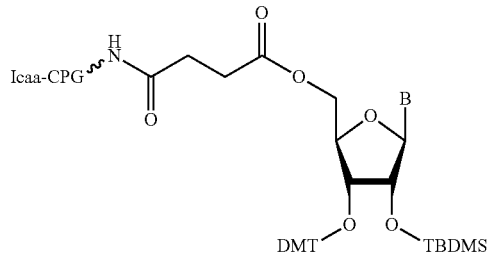

Where B = A (N-Bz), C (N-Bz), C (N-Ac), G (N-iBu),
A (N-tBPac), C (N-tBPac), C (N-tBPac), G (N-tBPac),
A (N-Pac), C (N-Pac), C (N-Pac), G (N-Pac), U.

3'-DMT-2'-tBDSilyl-5'-CPG
(Reverse RNA-tBDsilyl-5'-Icaa CPG)

Structure (18)

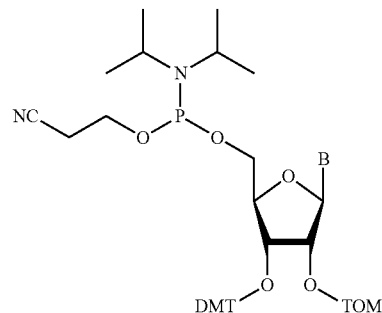

Where B = A (N-Ac), C (N-Ac), G (N-Ac), U.

3'-DMT-2'-TOM-(triisopropylsilyl oxymethylene)-5'-amidites
(Reverse RNA-TOM-5'-amidities)

The invention also teaches the method for preparing the disclosed compositions. The starting base protected nucleoside 19 affording isopropyliden protected nucleoside 20. Benzoylation followed by isopropyliden group removal yields 5'-benzolylated nucleoside 22. Consecutive silylation reaction with TBDMS chloride in pyridine provides mixture of 2'- and 3'-TBDMS protected nucleosides (23 and 24) in the ratio of 3:2 respectively. After column chromatography isomers have been resolved and isolated in % yield. Further reaction of the isomer 23 afforded 3'-DMT-2'-TBDMS protected nucleoside 26.

It is therefore conceivable that during subsequent functionalization of 3'-hydroxyl group, there will be significant migration of 2'-TBDMS group.

Scheme (I)

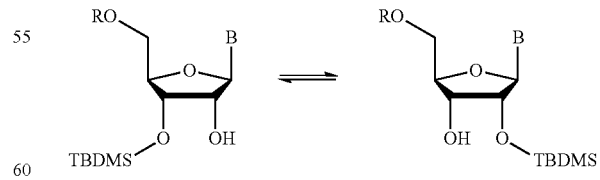

During the functionalization of 3'-hydroxyl group with DMT-(4,4-dimethoxytrityl), no significant migration was observed to occur. Moreover, the 3'-TBDMS protected isomer 24 also was involved in the same tritylation reaction as isomer 23 with DMT chloride in pyridine, however nucleoside 25 was not observed in that reaction. Therefore, in case of contamination of the 2'-TBDMS protected nucleoside 23 with its isomer 24, unwanted isomer 25 cannot be formed in the tritylation conditions and desired nucleoside 26 can be isolated in high purity. The 3'-TBDMS protected nucleoside 24 can be utilized in the synthesis of the desired product and converted into 23 due to isomerization process outlined in the scheme 1.

Removal of 5'-benzoyl group with sodium hydroxide in methanol followed by phosphitilation reaction using CEDP and DIPA tetrazolate affords the final reverse phosphoramidite 16.

on the left to the 3'-terminus on the right. The coupling efficiency of the 3'-DMT-5'-CED phosphoramidites indicated per step coupling surpassing 99%, leading to high purity RNA. A large number of homopolymers and 20-21-mers oligonucleotides have been synthesized using these monomer phosphoramidites.

Our data show that there is no difference in coupling efficiency during oligo synthesis using the reverse RNA monomers (for 5'→3'-direction) as compared to standard 3'-CED phosphoramidites in synthesis in 3'→5' direction.

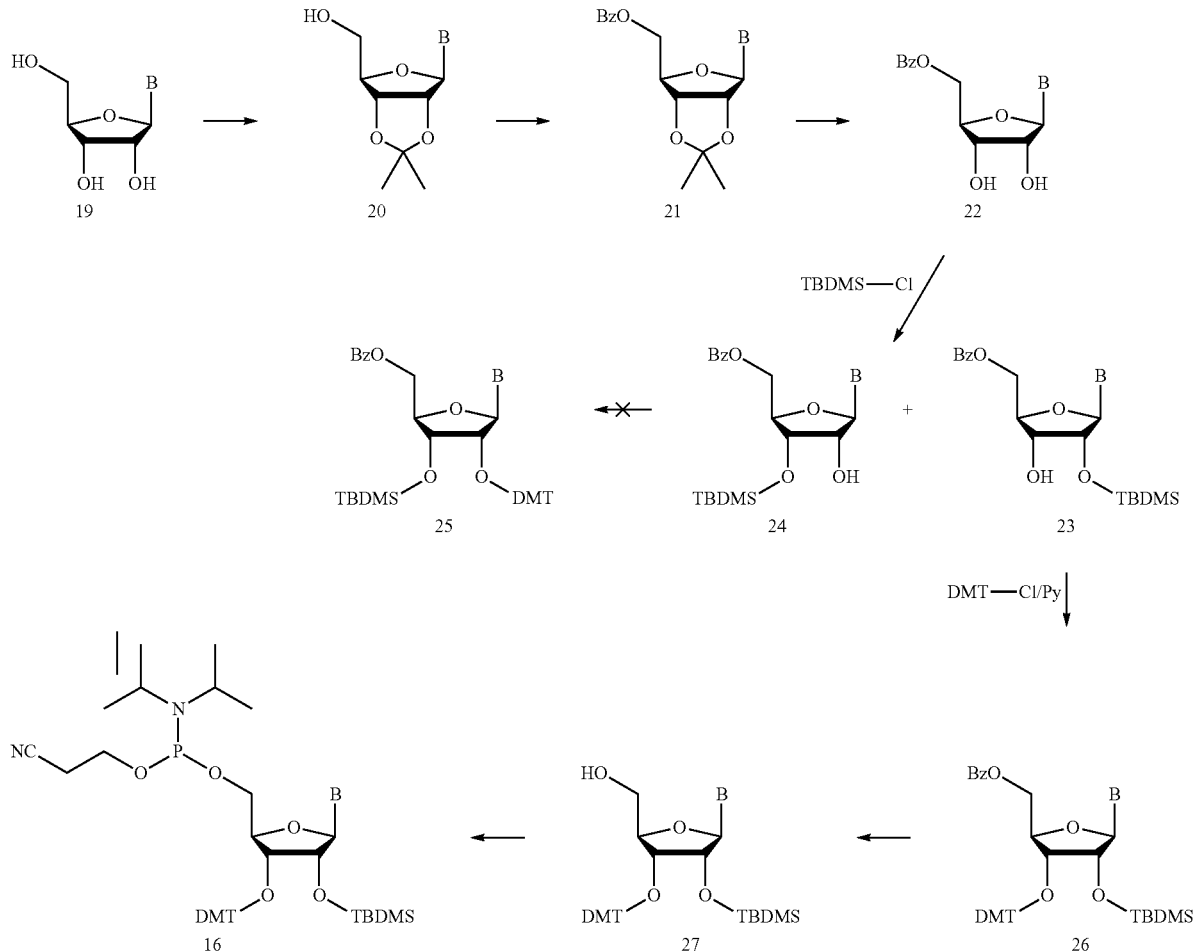

Scheme (2)

Where B = a) A (N-Bz), b) C (N-Bz), c) C (N-Ac), d) G (N-ibu)
e) A (N-tBPac), f) C (N-tBPac), g) G (N-tBPac),
h) A (N-Pac), i) C (N-Pac), j) G (N-Pac), k) U.

Oligonucleotide synthesis using reverse phosphoramidites was performed in the direction from 5'→3'.

The examples provided below further illustrate the invention; these are illustrative only and should not be construed as in any way limiting the scope of the invention. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus In another embodiment the invention provides method for synthesis of ribonucleic acid oligomers with modification or labeling of 3'-end of an oligonucleotide. The synthesis of 3'-end modified RNA requiring lipophilic, long chain ligands or chromophores fluorophores and quenchers can be performed using corresponding phosphoramidites. Our data show that 5'→3'-direction synthesis has very distinct advantage compared to conventional method.

In addition, the 3'-modifications that not available on solid support such as HEG or PEG-2000 can be easily introduced by using 5'→3'-direction synthesis and purified by reversephase HPLC. The oligonucleotide has been purified by RP HPLC, affording 95-98% pure products.

Experimental Examples

The notes below summarize the various innovations, advantages and possibilities, and some product and process details of the present invention. This list is meant to serve as a convenient and illustrative summary, and is not complete, exhaustive or limiting.

Derivatized nucleoside and phosphoramidites of general formula 1:

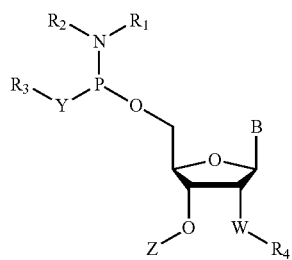

wherein
Y is oxygen or sulfur;
W is oxygen, nitrogen, sulfur or fluorine;
$R_4$ is silyl ether such as TBDMS, triisopropylsilyl oxymethylene, Fmoc, alkyl, aryl, or acetyl, when W is not sulphur; but in case when W is sulfur $R_4$ is benzoyl, acetyl or disulfide;
Z is DMT, MMT, TMT protecting group;
$R_1$ and $R_2$ are independently selected from an alkyl or aryl group;
$R_3$ is cyanoethyl, alkyl or aryl.

Derivatized nucleoside attached to solid support of general formula 2:

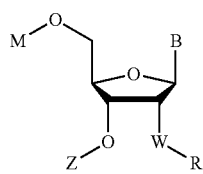

wherein
M is a hydrogen radical or Y—CO—;
Y is a chain of atoms from 2 to 20 in length, consisting essentially of a hydrocarbon chain optionally substituted by one or more heteroatoms independently selected from the group consisting of oxygen, nitrogen and sulfur, or any linker that is suitable for linking a solid support thereto, such as CPG, polystyrene or any other solid support suitable for oligonucleotide synthesis;
W is oxygen, nitrogen, sulfur or fluorine;
R is silyl ether such as TBDMS, triisopropylsilyl oxymethylene, Fmoc, alkyl, aryl, amino or acetyl, when W is not sulphur; but in the case when W is sulfur R is benzoyl, acetyl or disulfide;
Z is DMT, MMT, TMT protecting group.

A method for reverse, via 5' to 3' direction of oligonucleotide bond formations shown in formula 10 in synthetic RNA oligomers. The RNA could consist of natural or modified nucleo bases, gapmers, phosphodiesters, phosphorothiates, phosphoselenates. The synthesis may be performed on automated, semi automated DNA/RNA or other synthesizers or manually. The synthesis can be performed at various scales from microgram to kilogram scales.

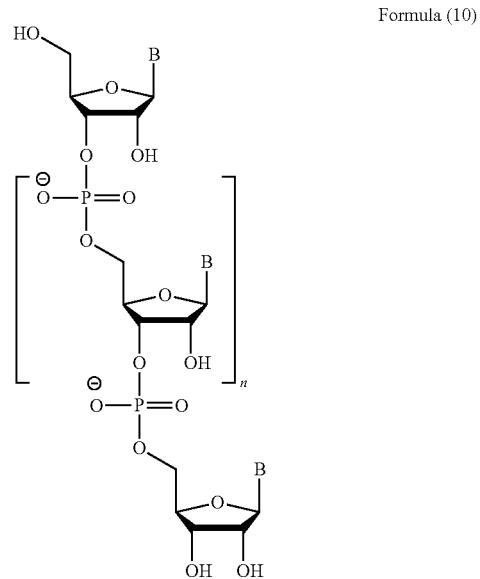

Formula (10)

A method of attachment of modifications to 3'-terminus of RNA molecules using corresponding phosphoramidites (Formula 11), wherein L is a modification such as biotin or cholesterol, or selected from the group consisting of fluorophore, quencher dyes, polyethylene glycols, and peptides.

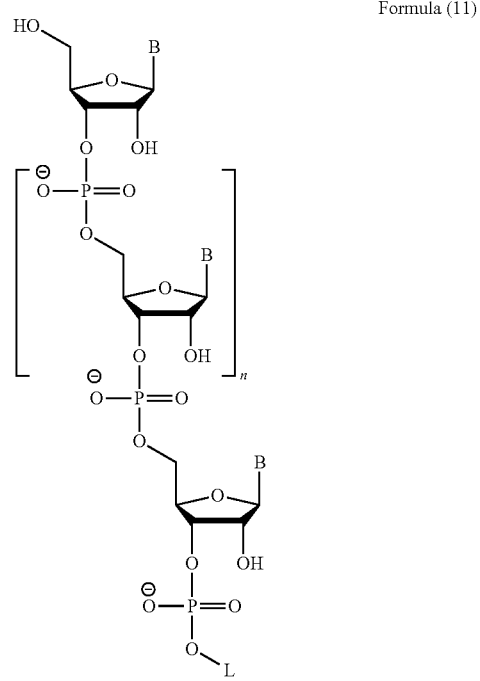

Formula (11)

Synthesis of automated high purity RNA using Reverse Direction (5'→3') RNA synthesis resulting in high purity RNA.

3'-Conjugation of RNA with macromolecules such as Cholesterol, hexaethyloxyglycols (HEG) and Polyethylene glycols (PEG).

Application of the automated RNA synthesis in the reverse Direction (5'→3') results in the absence of M+1 oligonucleotide impurities.

The modified nucleosides incorporated by this method mentioned above could consists of one or more of purine or pyrimidine modifications, such as but not limited to, 5-Fluoro-U, 5-Fluoro dU, 5-fluoro-dC, 5-Fluro-rC, pseudouridine, 5-methyl-dU, 5-methyl-rU, 5-methyl-dC, 5-methyl-rC, 5-bromo-dU, 5-bromo-rU, 5-bromo-dC, 5-bromo-rC, 5-iodo-dU, 5-iodo-rU, 5-vinyl-dU, 5-vinyl-rU, 5-vinyl thymidine, N-3 methyldeoxy uridine, N-3 methyl-ribouridine, N-3 methyl thymidine, 4-thio uridine, 4-thio-2'-deoxyuridine, 2,6-diaminopurine deoxy riboside, N-3 methyl ribothymidine, 2, 6-diaminopurine riboside, 8-bromo 2'-deoxy adenosine, 8-bromo-r-adenosine, 8-oxo-deoxy adenosine, 8-oxo-riboadenosine, 8-oxo-2'-deoxyadenosine, 8-oxo-riboadenosine, 8-oxo-deoxy inosine, 8-oxo-ribo inosine, 8-bromo-deoxy inosine, 8-bromo-ribo-inosine, N-1 methyl-riboadenosine, N-1 methyl-2'-deoxy adenosine, N-1 methyl 2'-deoxy inosine, N-1 methyl riboadenosine, N-1 methyldeoxy guanosine, N-1-methyl-riboguanosine, etheno adenosine, etheno 2'-deoxy adenosine, purine 2'-deoxy riboside, purine-ribonucleoside, 2-aminopurine-2'-deoxyriboside, 2-aminopurine-ribonucleoside.

Labelling of internal positions of an RNA synthesized by this method is achievable with chromophores such as, but not limited to Fluoroscein-C-5 dT, Dabcyl-C-5 thymidine, internal carboxyl group 5-dU-methylacrylate, biotin dT (biotin wattached via spacer to C-5 of dU), amino-dT (terminal amino attached via C-6 spacer to C-5 dU).

The sugar modification of modified nucleosides could consist of 2'-deoxy-2'-fluoro ribo nucleosides (2'-F-ANAs) such as A, C, G, U, Inosine and modified nucleosides containing 2'-Fluoro, in one or more positions of an RNA or DNA sequence synthesized by the method of this invention.

The sugar modification of modified nucleosides could consist of 2'-deoxy-2'-methoxy ribo nucleosides (2'-OMe-) such as A, C, G, U, Inosine and modified nucleosides containing 2'-methoxy, in one or more positions of an RNA or DNA sequence synthesized by this method.

The sugar modification of modified nucleosides could consist of 2'-deoxy-2'-amino ribo nucleosides (2'-NH2) such as A, C, G, U, Inosine and modified nucleosides containing 2'-amino, in one or more positions of an RNA or DNA sequence synthesized by this method.

The sugar modification of modified nucleosides could consist of 2'-deoxy-2'-terminal amino ribo nucleosides (2'-terminal NH2), attached via spacer from 2-10 atoms on nucleosides such as A, C, G, U, Inosine and modified nucleosides containing 2'-terminal amino, in one or more positions of an RNA or DNA sequence synthesized by this method.

The sugar modification of modified nucleosides could consist of 2'-deoxy-2'-methoxy ethoxy ribo nucleosides (2'-MOE), such as A, C, G, U, Inosine and modified nucleosides containing 2'-MOE, in one or more positions of an RNA or DNA sequence synthesized by this method.

The sugar modification of modified nucleosides could consist of other 2'-O-alkyl groups, such as 2'-deoxy-2'-ethoxy, propargyl, butyne ribo nucleosides (2'-OEt, O-Propargyl, 2'-O-Butyne), such as A, C, G, U, Inosine and modified nucleosides containing 2'-2'-OEt, O-Propargyl, 2'-O-Butyne, in one or more positions of an RNA or DNA sequence synthesized by this method.

The sugar modification of modified nucleosides could consist of 2'-deoxy-2'-fluoro arabino nucleosides (2'-F-ANAs) such as A, C, G, U, Inosine and modified nucleosides containing 2'-F-ANAs), in one or more positions of an RNA or DNA sequence synthesized by this method.

The sugar modification of modified nucleosides could consist of 2'-deoxy-2'-fluoro 4'-thioarabino nucleosides (4'-S-FANAs) such as A, C, G, U, Inosine and modified nucleosides containing 4'-S-FANAs in one or more positions of an RNA or DNA sequence synthesized by this method.

The RNA may be carried out with one or more 2'-5'-linkage within the sequence, at the 3'-end of the sequence or at the 5'-end of the sequence.

The RNA having a 3'-end, may be synthesized by the method of this invention containing reverse attached deoxy nucleosides such as dT, dC, dG, thymidine, attached via their 3'-hydroxyl function.

The RNA having a 3'-end may be synthesized by the method of this invention containing reverse attached ribonucleosides such as rA, rC, rG, rU, attached via their 2' or 3'-hydroxyl function.

The reverse RNA synthesis may be achieved comprising 2'-triisopropylsilyloxy methyl (TOM) protecting group.

The reverse RNA synthesis may be achieved comprising 2'-t-butyldithiom ethyl (DTM) protecting group.

The reverse RNA synthesis may be achieved comprising the modified base comprising 2'-deoxy-2'-fluoro-beta-D-arabinonucleic acid (FANA).

The reverse RNA synthesis may be achieved comprising the modified base comprising 4'-thio-2'-deoxy-2'-fluoro-beta-D-arabinonucleic acid (4'-Thio-FANA).

The reverse RNA synthesis may be achieved comprising the modified sugar using 2'-O-Methyl modification.

The reverse RNA synthesis may be achieved by using Bicyclic locked nucleic acids (LNA's).

The reverse RNA synthesis may use the modified sugar comprising altritol sugar modified oligonucleotides (ANA).

The reverse RNA synthesis may comprise the step of conjugation of lipophilic or hydrophobic groups at the 3'-end of the RNA either through a amidite function on the hydrophobic moiety or through an amino linker at the 3'-end of reverese synthesized oligonucleotide having a terminal amino group. The later synthesis involving a coupling step between amino at the 3'-terminal of oligonucleotide and carboxylic function on the lipophilic moiety. The lipophilic moieties consist of various glycol, such as triethylene glycol, hexaethylene glycol, polyethylene glycols, various lipids.

The reverse RNA synthesis may comprise the step of conjugation of peptides, such as cell penetrating peptides (CPPs) or membrane permeant peptide (MPPs) utilizing either the free amine function of such peptides and a 3'-terminal carboxylic function on the reverse synthesized RNA. The CPPs and MPPs having an appropriate carboxyl function can be coupled to the free terminal amino function of a 3'-end of the reverse synthesized RNA.

The reverse RNA synthesis comprise the 2'-5'-linked DNA units or 2'-5'-RNA units within the sequence, at the 3'-end of the sequence or at the 5'-end of the sequence.

Those skilled in the art will recognize, or be able to ascertain using no more than routine experimentation, many equivalents of the specific embodiments of the invention described herein. Such equivalents are encompassed by the following claims. Any combination of the embodiment disclosed in the dependent claims will also be contemplated to be within the scope of the invention.

The invention provides several advantages. First, the RNA synthesis in the reverse direction, that is, from the 5' to the 3' direction, would result in RNA oligonucleotides that are free of the M+1 impurities that are present in the RNA synthesis in the 3' to 5' direction. M+1 species arises when the synthesis does not stop at the intended number (M) of monomers, but proceeds to the unintended number (M+1) monomers. Second, the crude RNA purity ranges between 89% t 93%, which implies to a coupling efficiency of about 99.5% per step. Third, a single purification of the crude RNA results in 95%-98% pure oligonucleotides. Fourth, the invention enables the synthesis the long RNA that are useful to many aspects of biomedical research.

What is claimed is:

1. A process of synthesizing an RNA oligonucleotide of the following formula:

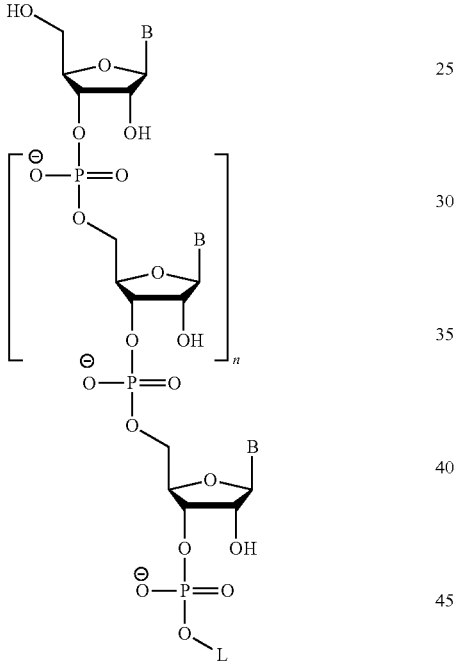

wherein:
B is a member selected from the group consisting of adenine, cytosine, guanine, uracil, 6-oxopurine, 5-methyl-cytosine, 5-methyl-uracil, 5-fluro-uracil, 7-deaza-adenine, 7-deaze-adenine and 5-fluro-cytosine;
n is an integer from 100 to about 200;
L is a nucleoside, or a non-nucleoside ligand wherein the non-nucleoside ligand is a member selected from the group consisting of cholesterol with a linker or a spacer, biotin, ethyleneglycol, glycerol, a polyethyelenglycol, a hexaehtyleneglycol, an amino linker, a disulfide linker, a peptide linker, a polypeptide linker, a protein, a flurophore, a quencher dye, one or more 2',5'-linked deoxynucleoside unit, one or more 2',5'-linked ribonucleoside unit, and one or more 2',5'-linked deoxyribose unit,
wherein L is attached at the 3'-end of the RNA nucleotide through an intervening phosphate; and the process of synthesizing the RNA oligonucleotide is in a direction from the 5'-end to the 3'-end of the RNA nucleotide, and the process comprises the steps of:
(a) taking a nucleoside solid support represented by Formula 2:

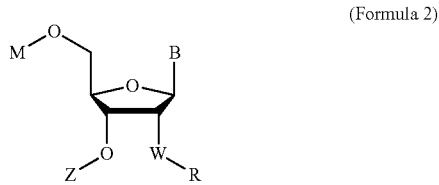

wherein:
M is a linker represented by the formula Y—C(O) and optionally connected to a solid support suitable for oligonucleotide synthesis,
wherein Y is a hydrocarbon diradical moiety having a length between 2 carbons and 20 carbons, and Y is selected from the group consisting of alkyl, alkenyl, cycloalkyl, aryl, and aralkyl, and the hydrocarbon diradical moiety optionally comprises intervening —O—, —S—, —S(O)$_2$— —C(O)— and —NR$_6$— where R$_6$ is a hydrogen radical, or a substituted C$_1$ to C$_{20}$ alkyl or a substituted aralkyl;
W is selected from the group consisting of an oxygen diradical, an N—H diradical, and a fluorine radical, and R is selected so that:
if W is an oxygen diradical, then R is tert butyl dimethyl silyl (TBDMS) or triisopropylsilyl oxymethylene (TOM); and
if W is an N—H diradical, then R is of the form R$_5^x$, where x is selected from the group consisting of fluorenylmethyloxycarbonyl (Fmoc), trifluoroacetyl, acetyl, alkanoyl and aroyl; and
if W is a fluorine radical, then R is not present;
B is selected from the group consisting of nucleoside base radicals consisting of 9-(N$^6$-benzoyladeninyl)-, 9-(N$^6$-acetyladeninyl)-, 9-(N$^6$-tert-butyl phenoxyacetyladeninyl)-, 9-(N$^6$-phenoxyacetyladeninyl)-, 9-(N$^6$-isopropyl phenoxyacetyladeninyl)-, 1-(N$^6$—(N,N-dimethylformamidinyl)adeninyl), 1-(N$^4$-benzoylcytosinyl)-, 1-(N$^4$-acetylcytosinyl)-, 1-(N$^4$—(N, N-dimethylformamidinyl)cytosinyl)-, 1-(N$^4$-phenoxyacetylcytosinyl)-, 1-(N$^4$-tert-butylphenoxyacetylcytosinyl)-, 1-(N$^4$-isopropyl phenoxyacetylcytosinyl)-, 9-($N^2$-isobutylguaninyl)-, 9-($N^2$-tert butyl phenoxyacetylguaninyl)-, 9-($N^2$-isopropyl phenoxyacetylguaninyl)-, 1-($N^4$-phenoxyacetylcytosinyl)-, 1-($N^4$-tert butyl phenoxyacetylcytosinyl)-, 1-($N^4$-isopropyl phenoxyacetylcytosinyl)-, and 1-uracilyl-; or B is a modified nucleoside base radical selected from the consisting of 1-($N^4$-benzoyl-5-methylcytosinyl)-, 1-($N^4$—(N,N-dimethylformamidinyl)-5-methylcytosinyl)-, 1-($N^4$-acetyl-5-methylcytosinyl)-, 1-(5-methyl-uracilyl)-, 1-(5-fluoro-uracilyl)-, 1-($N^4$-benzoyl-5-fluorocytosinyl)-, 9-($N^6$-benzoyl-7-deazaadeninyl)-, 9-($N^6$—(N,N-dimethylformamidinyl)-7-deazaadenyl)-, 9-($N^2$-isobutyl-7-deazaguaninyl)-, and 9-($N^2$—(N,N-dimethylformamidinyl)-7-deazaguaninyl)-;

Z is a member selected from the group consisting of dimethoxy triphenyl (DMT), monomethoxy triphenyl (MMT) and trimethoxy triphenyl (TMT);

(b) placing a phosphoramidite represented by Formula 1 on a oligonucleotide synthesizer;

(Formula 1)

wherein

Y is an oxygen atom or a sulfur atom;

W is selected from the group consisting of an oxygen diradical, an N—H diradical, and a fluorine radical; and $R_4$ is selected so that:

if W is an oxygen diradical, then $R_4$ is tert butyl dimethyl silyl (TBDMS) or triisopropylsilyl oxymethylene (TOM); and if W is an N—H diradical, then $R_4$ is of the form $R_5^x$, where x is selected from the group consisting of fluorenylmethyloxycarbonyl (Fmoc), trifluoroacetyl, acetyl, alkanoyl and aroyl; and if W is a fluorine radical, then $R_4$ is not present;

B is selected from the group consisting of nucleoside base radicals consisting of 9-($N^6$-benzoyladeninyl)-, 9-($N^6$-acetyladeninyl)-, 9-($N^6$-tert-butyl phenoxyacetyladeninyl)-, 9-($N^6$-phenoxyacetyladeninyl)-, 9-($N^6$-isopropyl phenoxyacetyladeninyl)-, 1-($N^6$—(N,N-dimethylformamidinyl)adeninyl), 1-($N^4$-benzoylcytosinyl)-, 1-($N^4$-acetylcytosinyl)-, 1-($N^4$—(N,N-dimethylformamidinyl)cytosinyl)-, 1-($N^4$-phenoxyacetylcytosinyl)-, 1-($N^4$-tert-butylphenoxyacetylcytosinyl)-, 1-($N^4$-isopropyl phenoxyacetylcytosinyl)-, 9-($N^2$-isobutylguaninyl)-, 9-($N^2$-tert butyl phenoxyacetylguaninyl)-, 9-($N^2$-isopropyl phenoxyacetylguaninyl)-, 1-($N^4$-phenoxyacetylcytosinyl)-, 1-($N^4$-tert butyl phenoxyacetylcytosinyl)-, 1-($N^4$-isopropyl phenoxyacetylcytosinyl)-, and 1-uracilyl-; or B is a modified nucleoside base radical selected from the consisting of 1-($N^4$-benzoyl-5-methylcytosinyl)-, 1-($N^4$—(N,N-dimethylformamidinyl)-5-methylcytosinyl)-, 1-($N^4$-acetyl-5-methylcytosinyl)-, 1-(5-methyl-uracilyl)-, 1-(5-fluoro-uracilyl)-, 1-($N^4$-benzoyl-5-fluorocytosinyl)-, 9-($N^6$-benzoyl-7-deazaadeninyl)-, 9-($N^6$—(N,N-dimethylformamidinyl)-7-deazaadenyl)-, 9-($N^2$-isobutyl-7-deazaguaninyl)-, and 9-($N^2$—(N,N-dimethylformamidinyl)-7-deazaguaninyl)-;

Z is a member selected from the group consisting of dimethoxy triphenyl (DMT), monomethoxy triphenyl (MMT) and trimethoxy triphenyl (TMT);

$R_1$ is an alkyl or aryl radical;

$R_2$ is an alkyl or aryl radical; and $R_3$ is cyanoethyl, alkyl or aryl radical;

B is hydrogen or a nucleobase that is optionally functionalized at each primary amine with an amine protecting group;

(c) removing the protecting group Z from the nucleoside solid support represented by Formula 2;

(d) performing the process of RNA synthesis by coupling the nucleoside of Formula 2 and the phosphoramidite of Formula 1 in the oligonucleotide synthesizer using a mixture of ancillary regents to result in an oligonucleotide having at least one protecting group;

(e) providing a phosphoramidite with the L group;

(f) adding the phosphoramidite with the L group at the end of the oligonucleotide to result in an oligonucleotide having the L group;

(g) detaching the oligonucleotide having the L group from the solid support;

(h) removing the at least one protecting group from the oligonucleotide;

(i) removing a silyl protecting group to result in the oligonucleotide;

(j) participating the oligonucleotide; and (k) analyzing the oligonucleotide for purity determination, wherein the mixture of ancillary reagent in step (d) comprises phenoxy acetic anhydride/tetrahydrofuran/pyridine), 10% N-methylimidazole/tetrohydrofuran), 3% trichloroacetic acid in toluene, 0.05 M iodine/pyridine/water/tetrahyrofuran and 5-ethylthio-1-H-tetrazole at 0.35 M in acetonitrile.

2. The process according claim 1, wherein L is cholesterol with the linker or the spacer, and n is an integer from 100 to about 200.

3. The process according to claim 1, wherein L is polyethyleneglycol, and n is an integer from 100 to about 200.

4. An RNA oligonucleotide, wherein the RNA oligonucleotide is synthesized by the process according to claim 1.

5. A method of RNA synthesis of 100-200-mer long chain RNA using reverse RNA synthesis methodology according to claim 1.

6. A long chain RNA chimera, comprising deoxy, backbone-modified bases, modified DNA and modified RNA bases, wherein the long chain RNA chimera is synthesized according to the process of claim 1.

7. A long chain RNA having one or more 5',2', 2',3' linkage at the terminals, at a branch point or within the long chain RNA, wherein the long chain RNA is synthesized according to the process of claim 1.

8. A long chain RNA consisting of natural and modified nucleosides, abasic sites, reverse abasic sites, chromophores and ligand, wherein the long chain RNA is synthesized according to the process of claim 1.

9. A long chain RNA comprising a chromophore, a ligand, a monophosphate group, a diphosphate group or a triphosphate group, wherein the long chain RNA is synthesized according to the process of claim 1.

10. A long chain RNA having a branch point with one or more deoxy, modified deoxy or modified ribonucleoside, wherein the long chain RNA is synthesized according to the process of claim 1.

11. The process according to claim 1, further comprising the step of purifying the RNA oligonucleotide using an HPLC Gel electrophoresis or an RNA purification technique.

12. A method of labeling and attaching a long chain RNA to a surface, comprising the steps of:
- introducing an amine function to the 3'-end of the long chain RNA;
- introducing an aldehyde function to the surface; and
- attaching the amine function to the aldehyde function, wherein the long chain RNA is synthesized according to the process of claim 1.

* * * * *

SEQUENCE LISTING

```
<160> NUMBER OF SEQ ID NOS: 7

<210> SEQ ID NO 1
<211> LENGTH: 100
<212> TYPE: RNA
<213> ORGANISM: Artificial Sequence
<220> FEATURE:
<223> OTHER INFORMATION: Completely Synthesized

<400> SEQUENCE: 1
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa                             100

<210> SEQ ID NO 2
<211> LENGTH: 150
<212> TYPE: RNA
<213> ORGANISM: Artificial Sequence
<220> FEATURE:
<223> OTHER INFORMATION: Completely Synthesized

<400> SEQUENCE: 2
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa                                       150

<210> SEQ ID NO 3
<211> LENGTH: 200
<212> TYPE: RNA
<213> ORGANISM: Artificial Sequence
<220> FEATURE:
<223> OTHER INFORMATION: Completely Synthesized

<400> SEQUENCE: 3
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa                                                  200

<210> SEQ ID NO 4
<211> LENGTH: 31
<212> TYPE: RNA
<213> ORGANISM: Artificial Sequence
<220> FEATURE:
<223> OTHER INFORMATION: Completely Synthesized
<220> FEATURE:
<221> NAME/KEY: modified_base
<222> LOCATION: (15)..(15)
<223> OTHER INFORMATION: At position 15, modified base um
```

```
<220> FEATURE:
<221> NAME/KEY: modified_base
<222> LOCATION: (21)..(21)
<223> OTHER INFORMATION: At position 21, modified base um
<220> FEATURE:
<221> NAME/KEY: modified_base
<222> LOCATION: (31)..(31)
<223> OTHER INFORMATION: At position 31, modified base um

<400> SEQUENCE: 4
acgggaagag ggaaugaggg uacgagggcg u                              31

<210> SEQ ID NO 5
<211> LENGTH: 43
<212> TYPE: RNA
<213> ORGANISM: Artificial Sequence
<220> FEATURE:
<223> OTHER INFORMATION: Completely Synthesized
<220> FEATURE:
<221> NAME/KEY: modified_base
<222> LOCATION: (16)..(16)
<223> OTHER INFORMATION: Modified base at position 16 is um
<220> FEATURE:
<221> NAME/KEY: modified_base
<222> LOCATION: (17)..(19)
<223> OTHER INFORMATION: Modified base at positions 17 through 19 is gm
<220> FEATURE:
<221> NAME/KEY: modified_base
<222> LOCATION: (20)..(20)
<223> OTHER INFORMATION: Modified base at position 20 is cm
<220> FEATURE:
<221> NAME/KEY: modified_base
<222> LOCATION: (21)..(21)
<223> OTHER INFORMATION: Modified base at position 21 is
     2'-O-methyladenosine
<220> FEATURE:
<221> NAME/KEY: modified_base
<222> LOCATION: (22)..(23)
<223> OTHER INFORMATION: Modified base at positions 22 through 23 is cm
<220> FEATURE:
<221> NAME/KEY: modified_base
<222> LOCATION: (31)..(33)
<223> OTHER INFORMATION: Modified base at positions 31 through 33 is gm
<220> FEATURE:
<221> NAME/KEY: modified_base
<222> LOCATION: (34)..(34)
<223> OTHER INFORMATION: Modified base at position 34 is cm
<220> FEATURE:
<221> NAME/KEY: modified_base
<222> LOCATION: (35)..(35)
<223> OTHER INFORMATION: Modified base at position 35 is
     2'-O-methyladenosine
<220> FEATURE:
<221> NAME/KEY: modified_base
<222> LOCATION: (36)..(37)
<223> OTHER INFORMATION: Modified base at positions 36 through 37 is cm
<220> FEATURE:
<221> NAME/KEY: modified_base
<222> LOCATION: (38)..(38)
<223> OTHER INFORMATION: Modified base at position 38 is
     2'-O-methyladenosine

<400> SEQUENCE: 5
ggcccauccg uggagugggc accccccaggg gggcaccacg guc                43

<210> SEQ ID NO 6
<211> LENGTH: 74
<212> TYPE: RNA
<213> ORGANISM: Artificial Sequence
<220> FEATURE:
<223> OTHER INFORMATION: Completely Synthesized

<400> SEQUENCE: 6
uccucuguag uucagucggu agaacggcgg acuuucaauc cguaugucac ugguucgagu   60
```

```
ccagucagag gagc                                                     74

<210> SEQ ID NO 7
<211> LENGTH: 76
<212> TYPE: RNA
<213> ORGANISM: Artificial Sequence
<220> FEATURE:
<223> OTHER INFORMATION: Completely Synthesized

<400> SEQUENCE: 7
gcccggauag cucagucggu agagcaucag acuuuuuauc ugagggucca ggguucaagu    60
cccuguucgg gcgcca                                                   76
```